(12) United States Patent
Chae et al.

(10) Patent No.: US 10,889,609 B2
(45) Date of Patent: Jan. 12, 2021

(54) MANNITOL-BASED AMPHIPATHIC COMPOUND AND USE THEREOF

(71) Applicant: Industry-University Cooperation Foundation Hanyang University Erica Campus, Gyeonggi-do (KR)

(72) Inventors: Pil Seok Chae, Gyeonggi-do (KR); Hazrat Hussain, Gyeonggi-do (KR)

(73) Assignee: INDUSTRY-UNIVERSITY COOPERATION FOUNDATION HANYANG UNIVERSITY ERICA CAMPUS, Gyeonggi-Do (KR)

( * ) Notice: Subject to any disclaimer, the term of this patent is extended or adjusted under 35 U.S.C. 154(b) by 73 days.

(21) Appl. No.: 15/758,782

(22) PCT Filed: Dec. 14, 2015

(86) PCT No.: PCT/KR2015/013688
§ 371 (c)(1),
(2) Date: Mar. 9, 2018

(87) PCT Pub. No.: WO2017/043703
PCT Pub. Date: Mar. 16, 2017

(65) Prior Publication Data
US 2019/0077822 A1 Mar. 14, 2019

(30) Foreign Application Priority Data
Sep. 9, 2015 (KR) .......................... 10-2015-0127586

(51) Int. Cl.
| C07H 15/04 | (2006.01) |
| C07C 41/28 | (2006.01) |
| C07K 1/14 | (2006.01) |
| G01N 33/68 | (2006.01) |
| C07K 1/32 | (2006.01) |
| C07H 1/00 | (2006.01) |

(52) U.S. Cl.
CPC ............. *C07H 15/04* (2013.01); *C07C 41/28* (2013.01); *C07H 1/00* (2013.01); *C07K 1/14* (2013.01); *C07K 1/145* (2013.01); *C07K 1/32* (2013.01); *G01N 33/68* (2013.01); *G01N 33/6872* (2013.01); *Y02P 20/55* (2015.11)

(58) Field of Classification Search
CPC ................ C07H 15/04; C07C 41/28
See application file for complete search history.

(56) References Cited

U.S. PATENT DOCUMENTS

| 5,811,405 | A | * | 9/1998 | Toepfer ................... C07H 3/06 514/23 |
| 8,263,754 | B2 | | 9/2012 | Helmer et al. |
| 8,481,691 | B2 | | 7/2013 | Coleman et al. |
| 2010/0311956 | A1 | | 12/2010 | Gellman et al. |
| 2013/0005016 | A1 | | 1/2013 | Pucci et al. |

OTHER PUBLICATIONS

Chae, P. S. et al., Nature Methods, "Maltose-neopentyl glycol (MNG) amphiphiles for solubilization, stabilization and crystallization of membrane proteins", 2010, vol. 7, No. 12, pp. 1003-1011 (Year: 2010).*
Dumoulin, F. et al., Chem. Eur. J., "Synthesis and Liquid Crystalline Properties of Mono-, Di- and Tri-O-alkyl Pentaerythritol Derivatives Bearing Tri-, Di- or Monogalactosyl Heads: The Effects of Curvature of Molecular Packing on Mesophase Formation", 2007, vol. 13, pp. 5585-5600 (Year: 2007).*
Singh, M. et al., Journal of the Indian Institute of Science, "Carbohydrate-based liquid crystals", 2009, vol. 89, No. 2, pp. 113-135 (Year: 2009).*
Newstead, S. et al., "Insights into outer membrane protein crystallisation," Mol Membr Biol., 2010 ed., (vol. 25), (Issue. 8), (p. 631-638).
Newstead, S. et al., "Rationalizing α-helical membrane protein crystallization," Protein Science, 2008 ed., Cold Spring Harbor, (vol. 17), (p. 466-472).
Chae, P.S. et al., "New Ganglio-tripod Amphiphiles (TPAs) for Membrane Protein Solubilization and Stabilization: Implications for Detergent Structure-property Relationships", Organic & Biomolecular Chemistry, Nov. 14, 2014, vol. 12, No. 42, (p. 8480-8487).

* cited by examiner

*Primary Examiner* — Bahar Craigo
(74) *Attorney, Agent, or Firm* — Hammer & Associates, P.C.

(57) ABSTRACT

The present invention relates to a mannitol-based amphipathic compound, a method of preparing the same, a method of extracting, solubilizing, stabilizing or crystallizing a membrane protein using the compound, and a method of analyzing a structure of the membrane protein under an electron microscope using the compound. When the mannitol-based compound according to the present invention is used, the membrane protein can be stably stored in an aqueous solution for a prolonged period of time and thus can be applied to analysis of functions and structures thereof. Since the analysis of the structures and functions of the membrane protein is one of the fields of most interest in biology and chemistry currently, and more than half of new drugs currently in development are targeting membrane proteins, the present invention is applicable to research on the structures of membrane proteins closely related to the development of the new drugs.

7 Claims, 24 Drawing Sheets

[Figure 1]
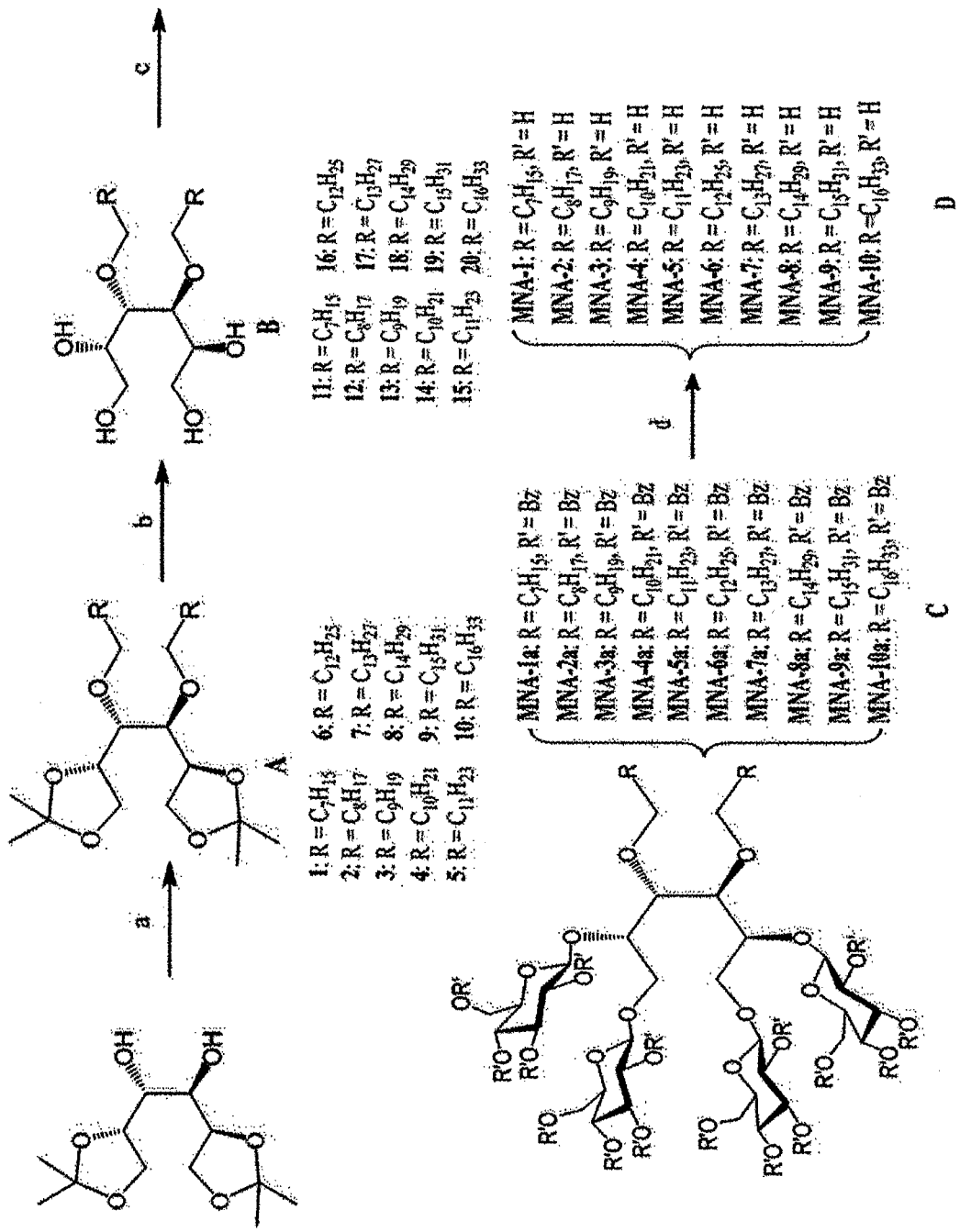

[Figure 2]
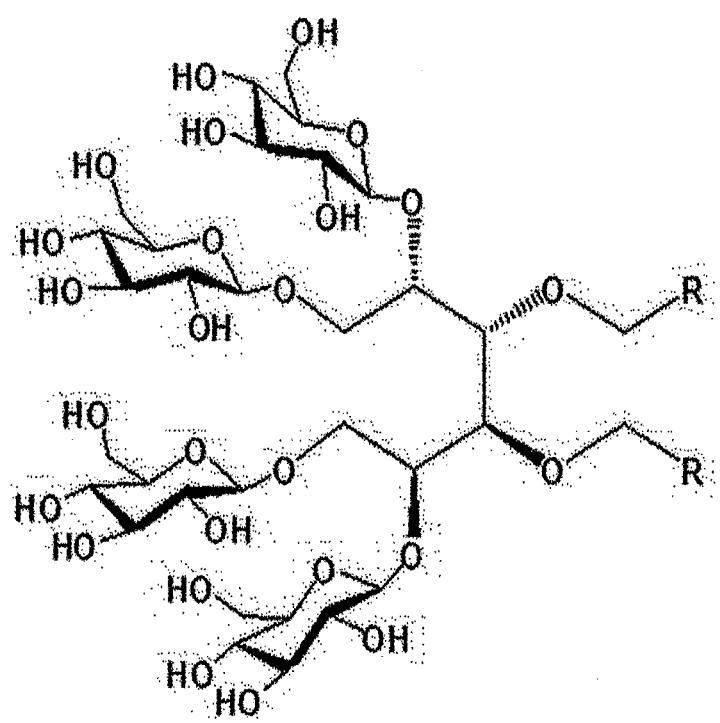
MNA-1 : R = n-C$_7$H$_{15}$
MNA-2 : R = n-C$_8$H$_{17}$
MNA-3 : R = n-C$_9$H$_{19}$
MNA-4 : R = n-C$_{10}$H$_{21}$
MNA-5 : R = n-C$_{11}$H$_{23}$
MNA-6 : R = n-C$_{12}$H$_{25}$
MNA-7 : R = n-C$_{13}$H$_{27}$
MNA-8 : R = n-C$_{14}$H$_{29}$
MNA-9 : R = n-C$_{15}$H$_{31}$
MNA-10 : R = n-C$_{16}$H$_{33}$

[Figure 3]
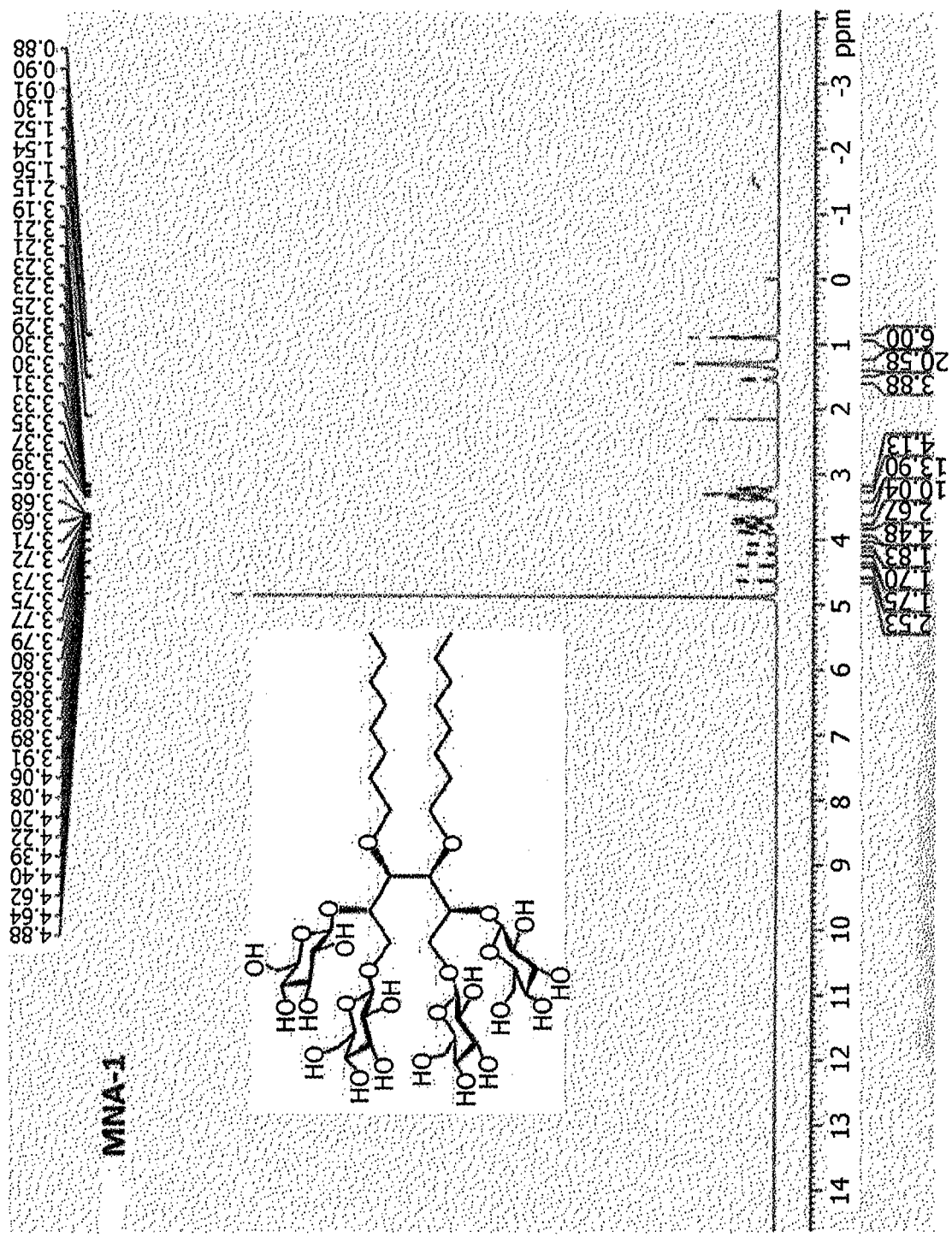

[Figure 4]
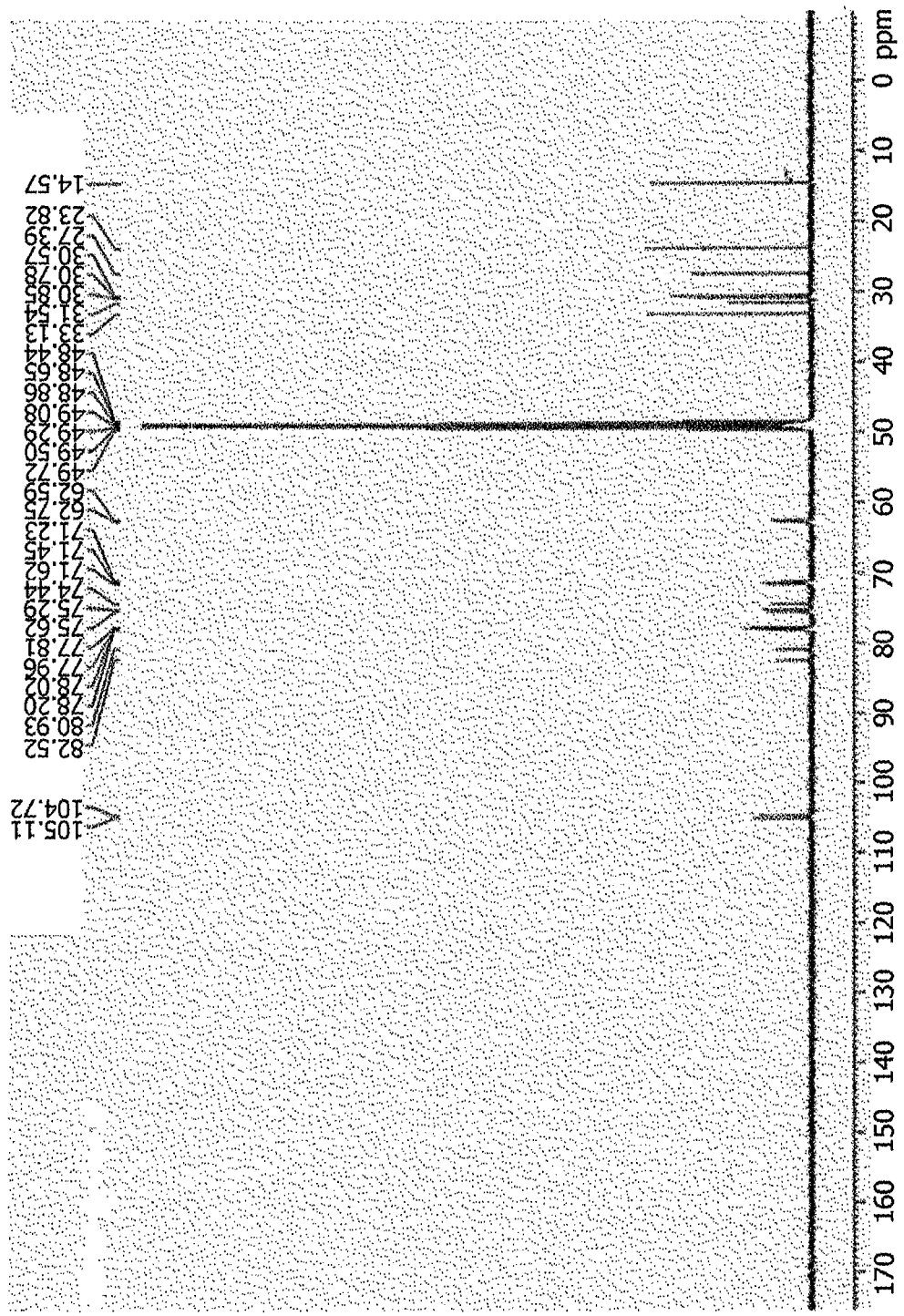

【Figure 5】
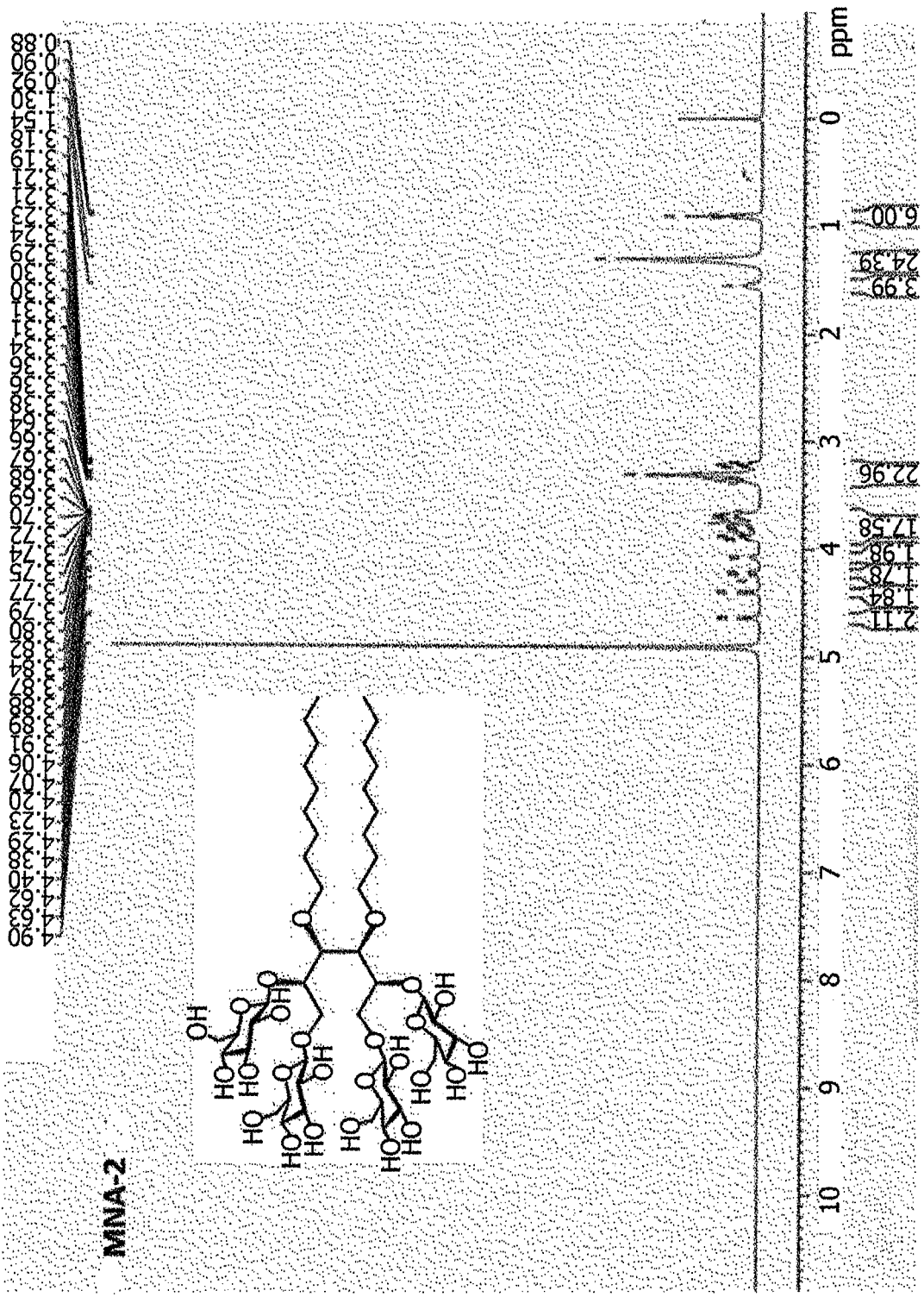

【Figure 6】
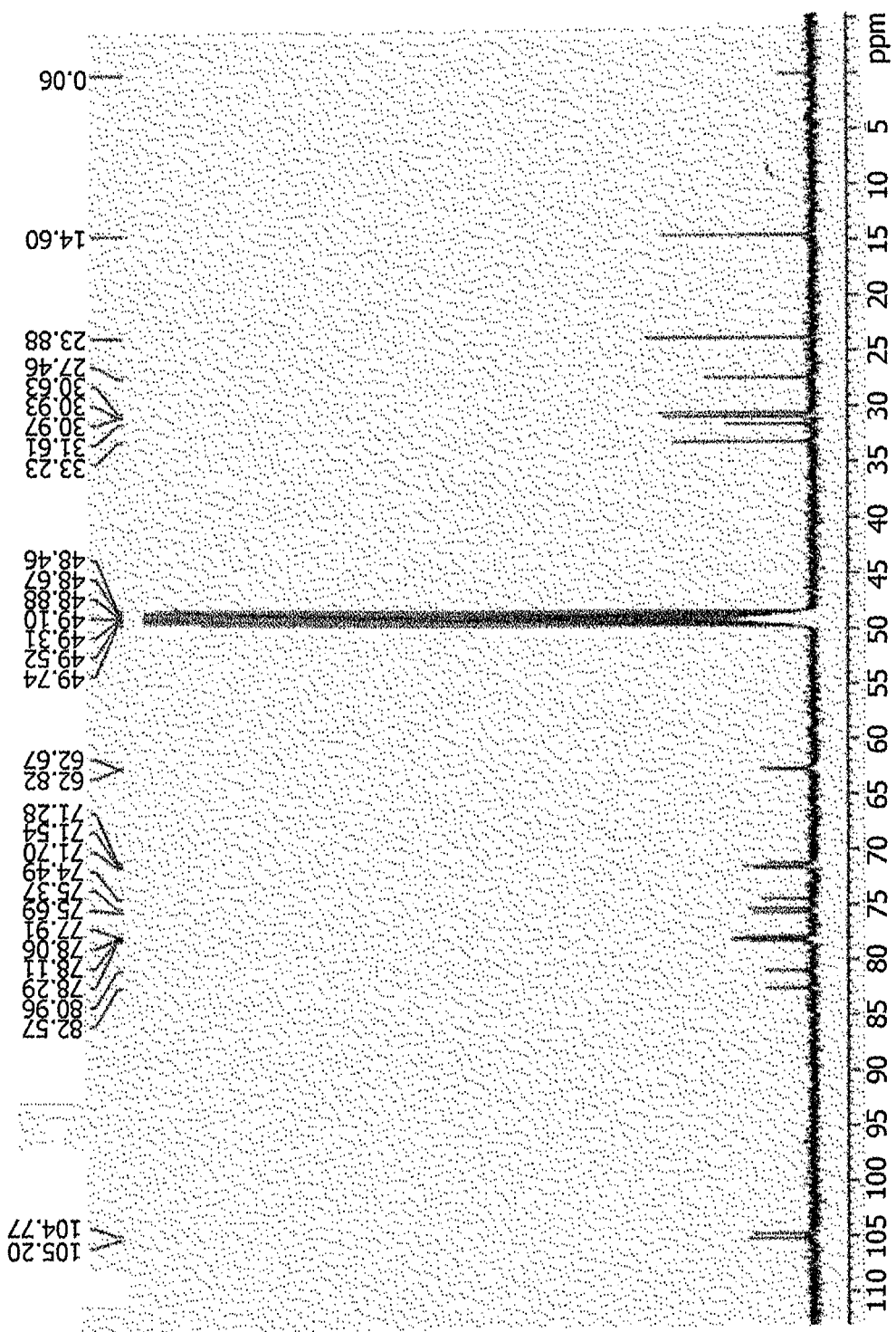

[Figure 7]
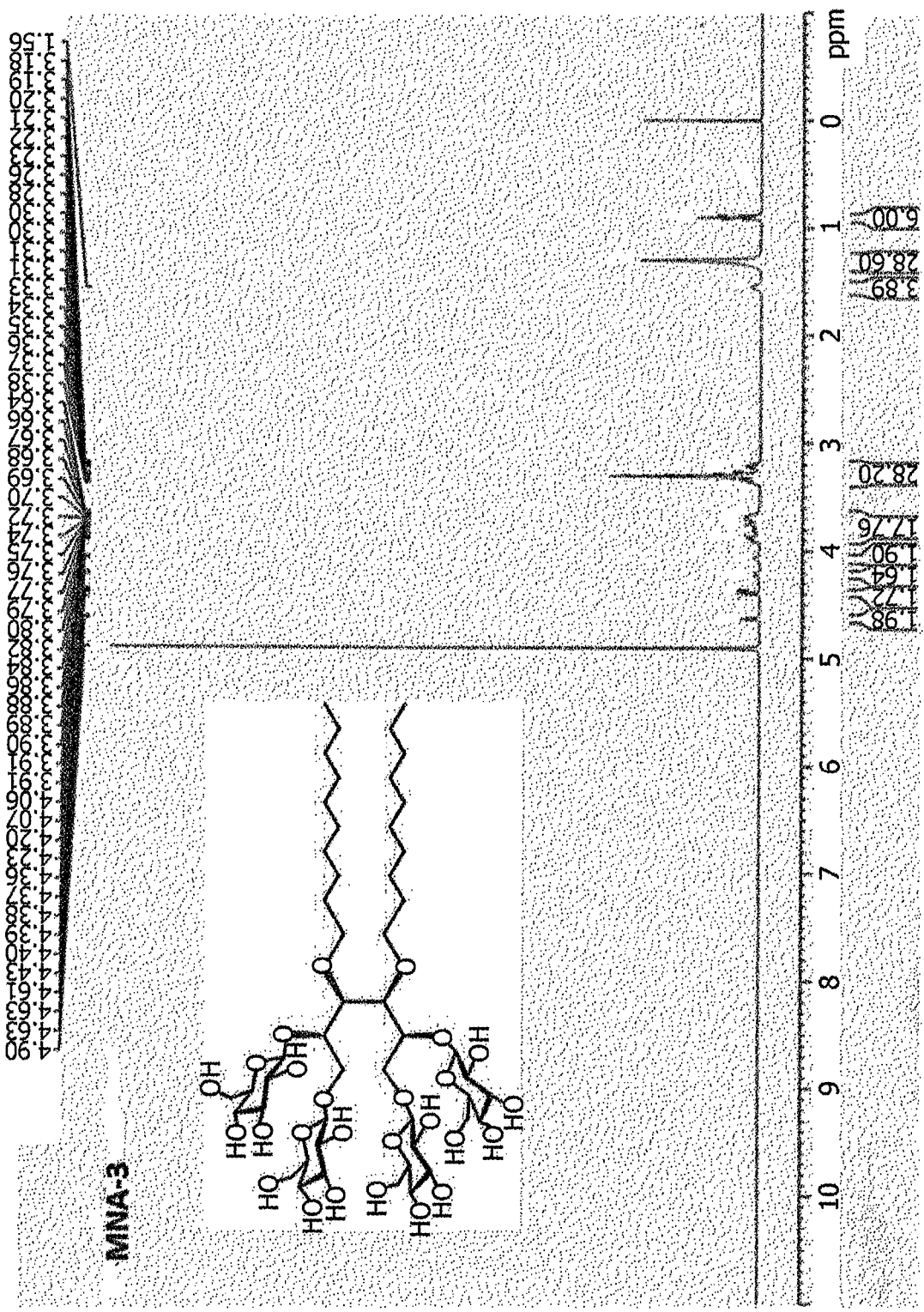

[Figure 8]
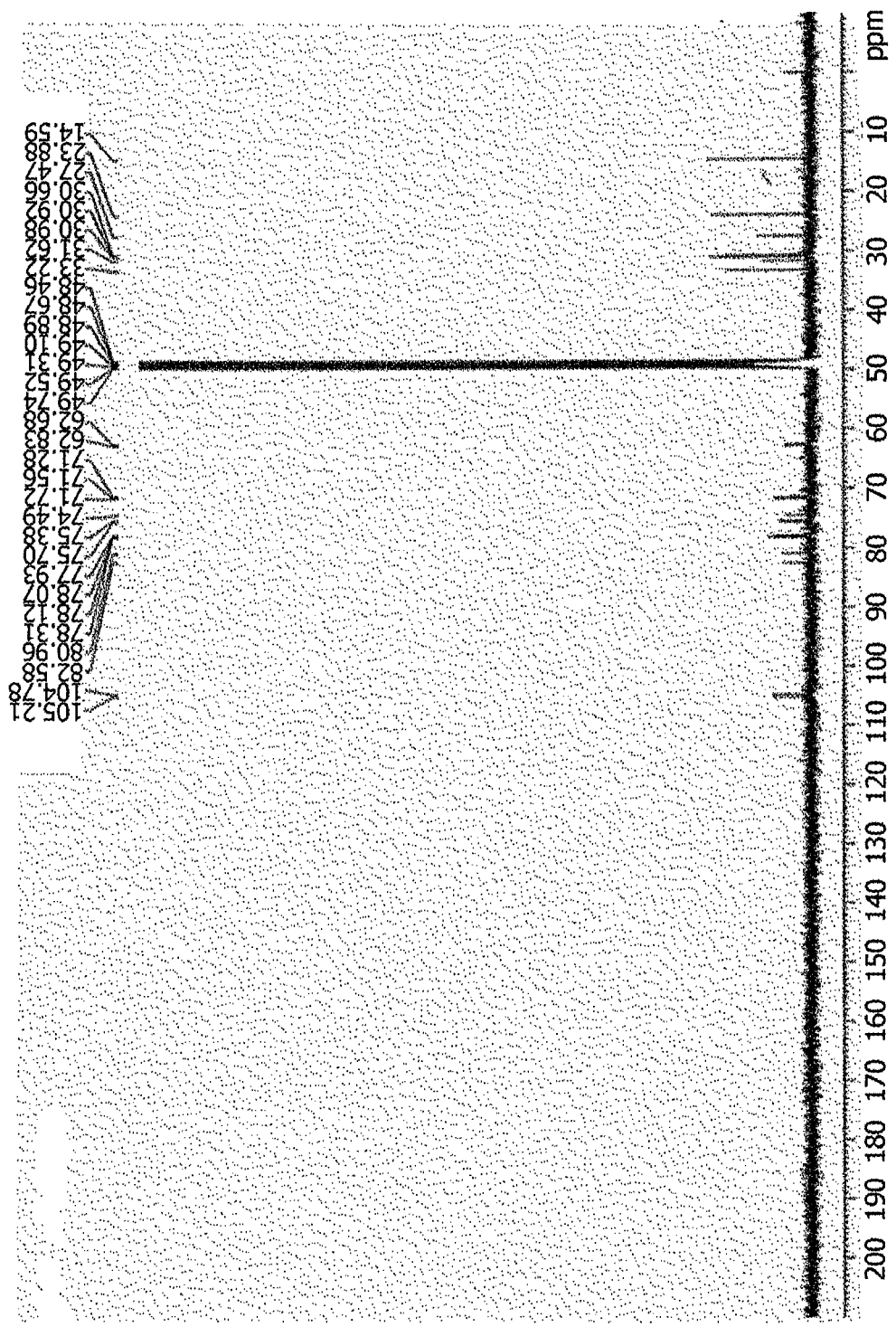

[Figure 9]
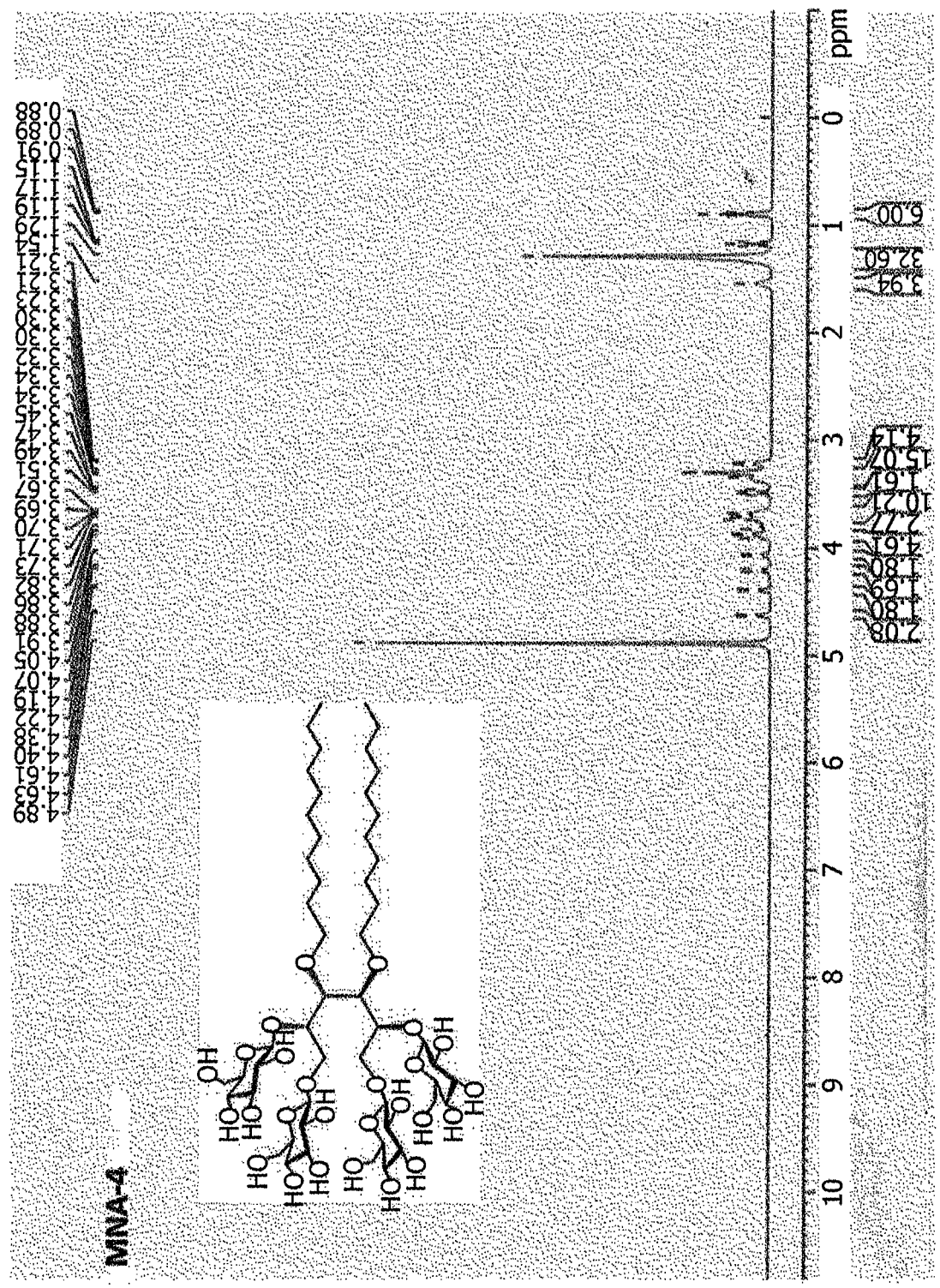

[Figure 10]

[Figure 11]
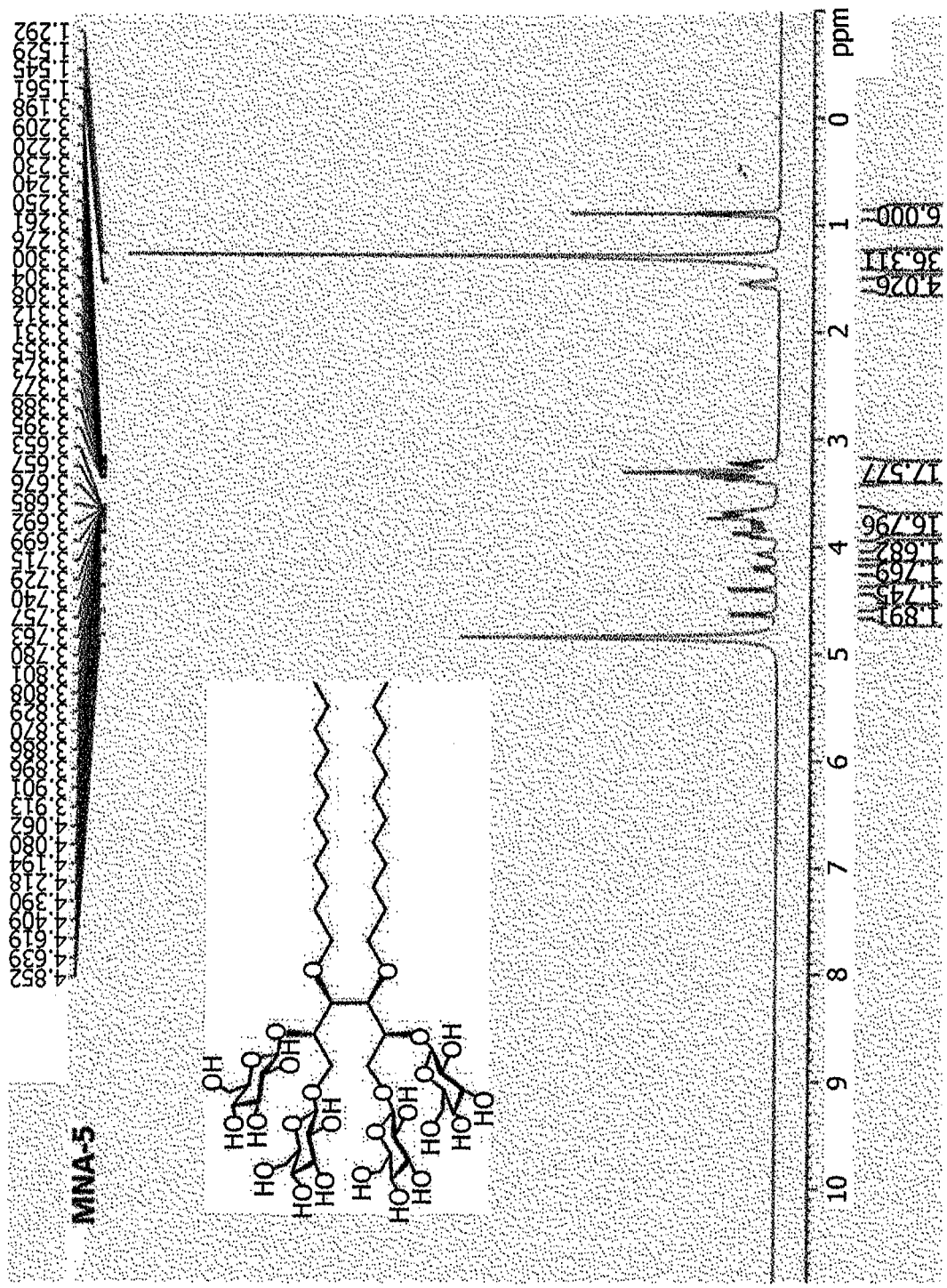

[Figure 12]
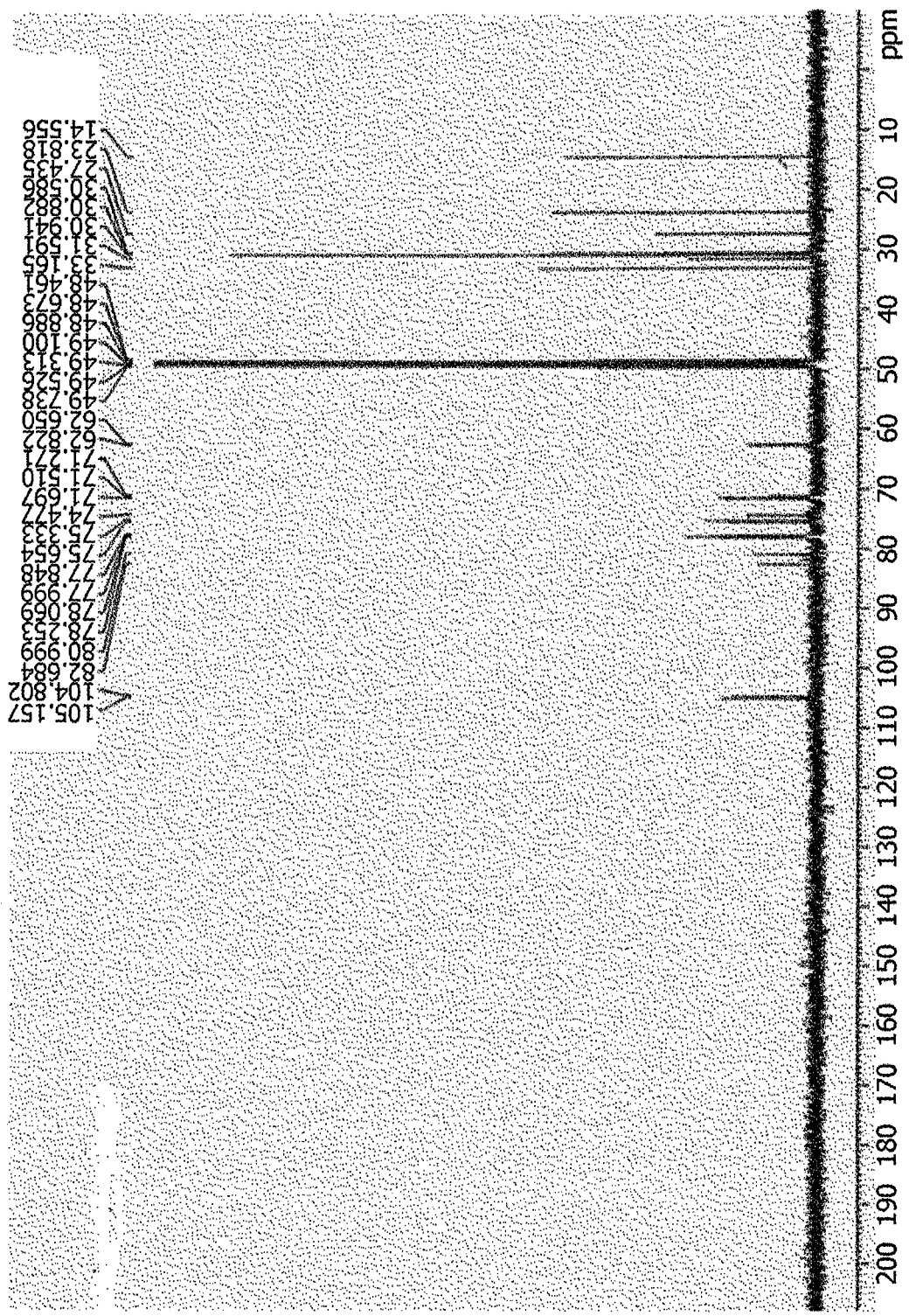

[Figure 13]
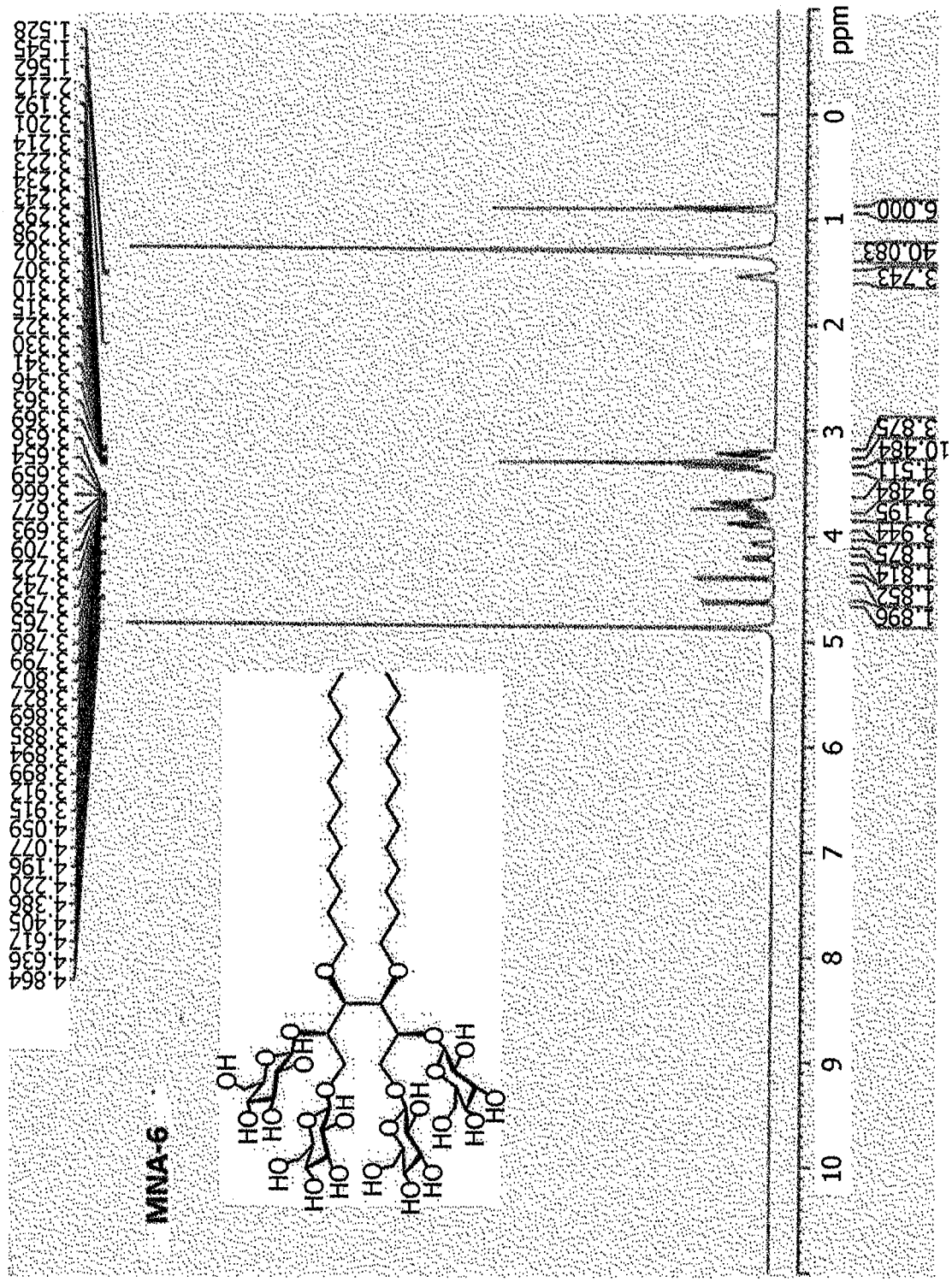

[Figure 14]
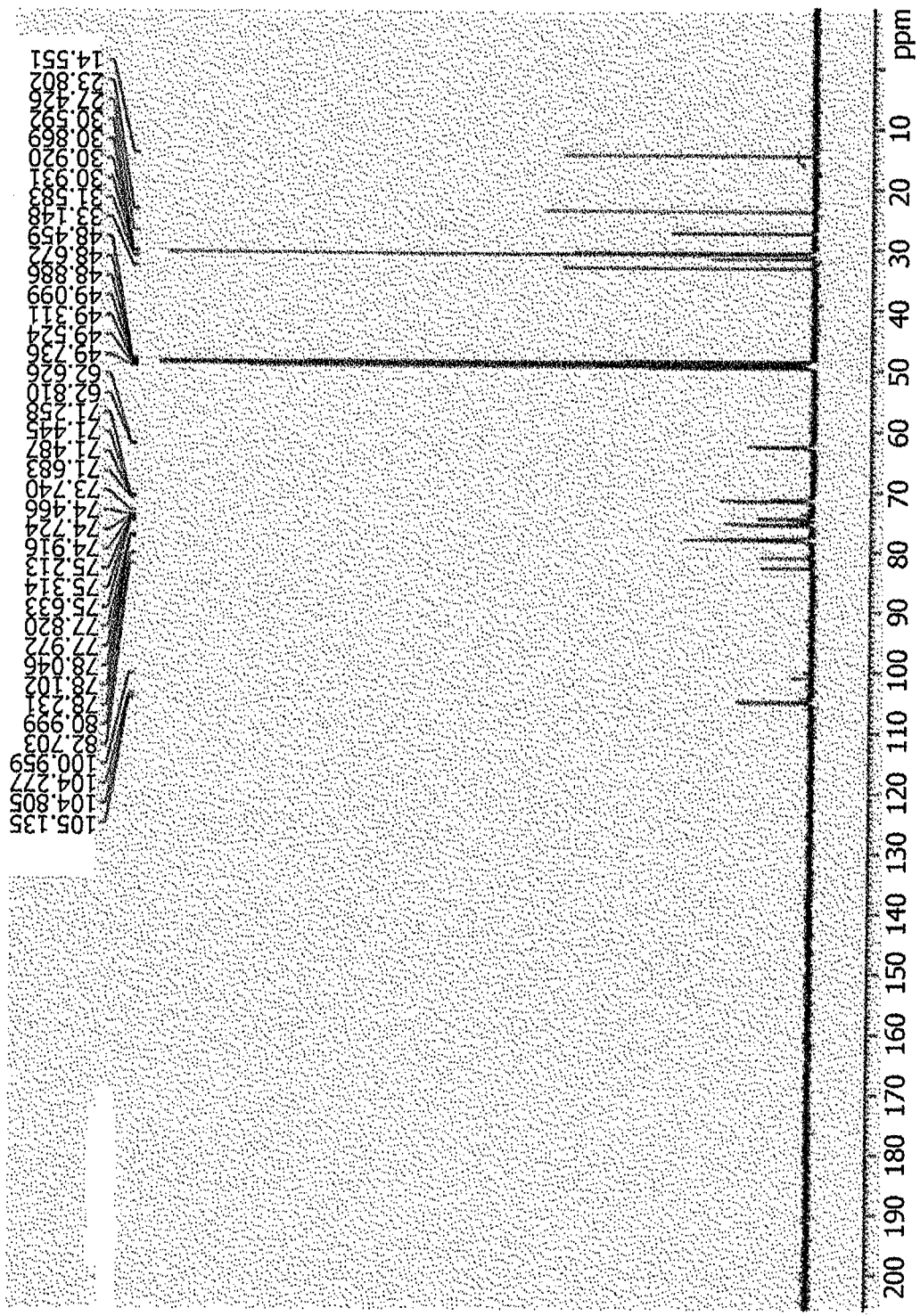

[Figure 15]
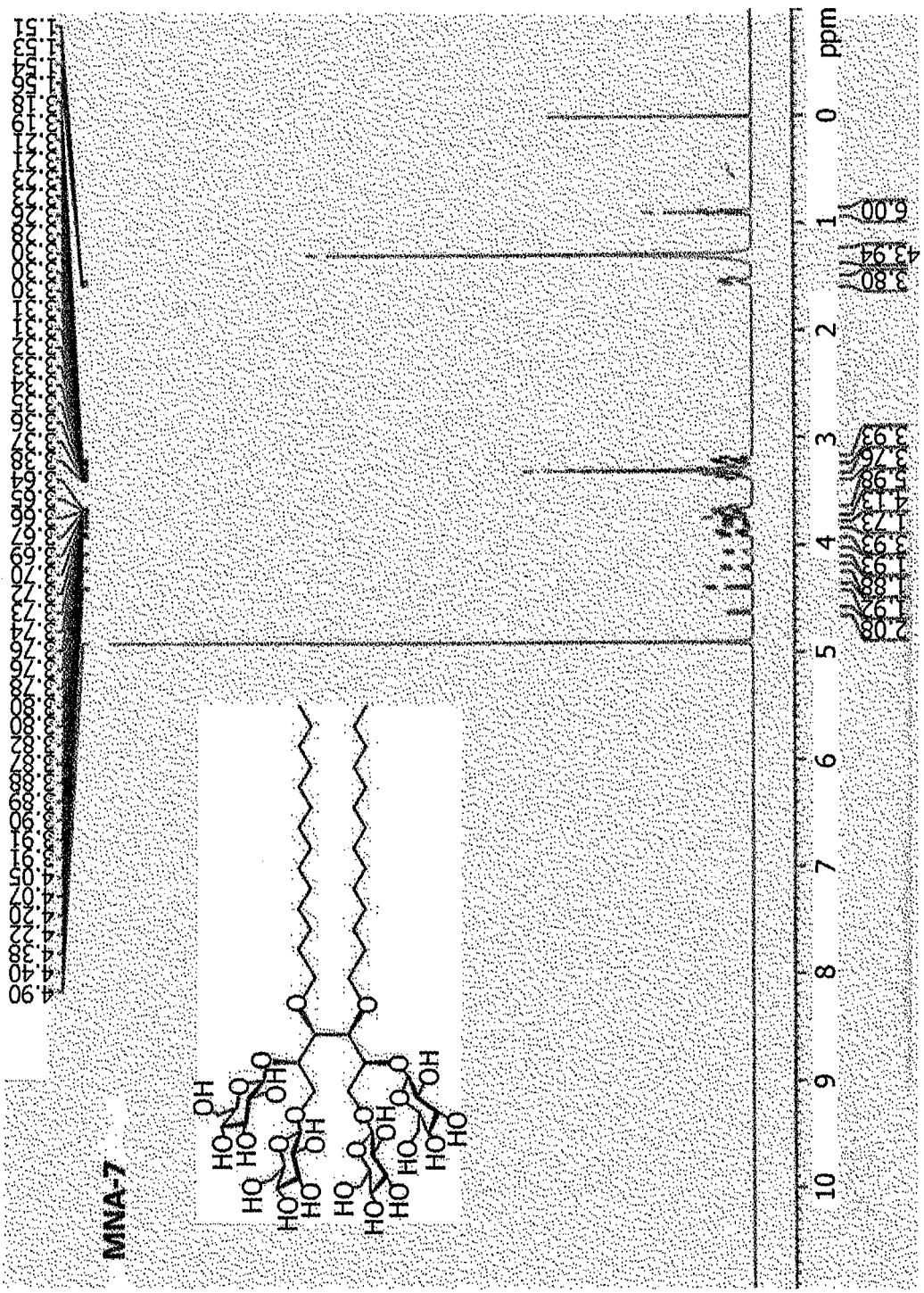

[Figure 16]
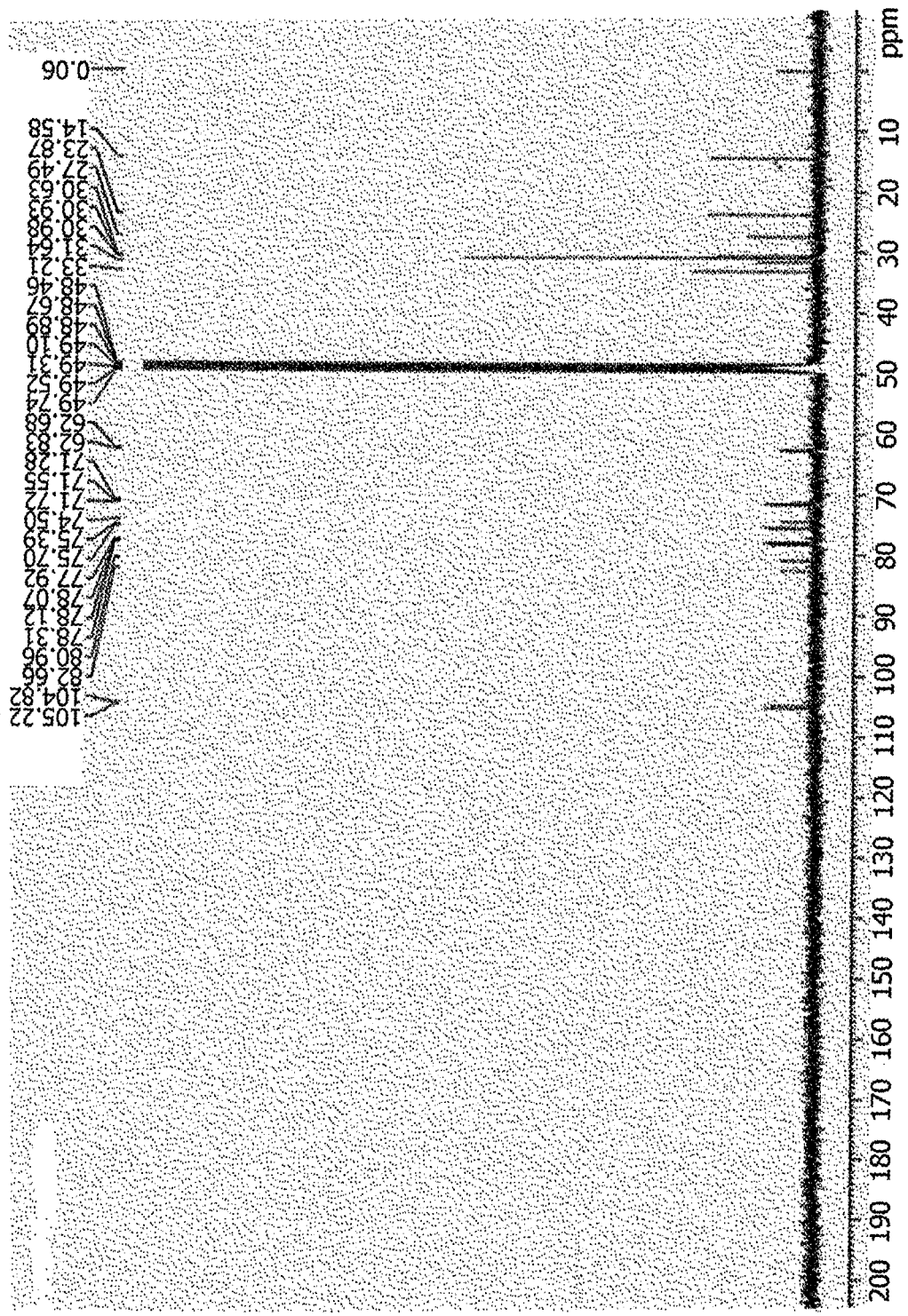

[Figure 17]
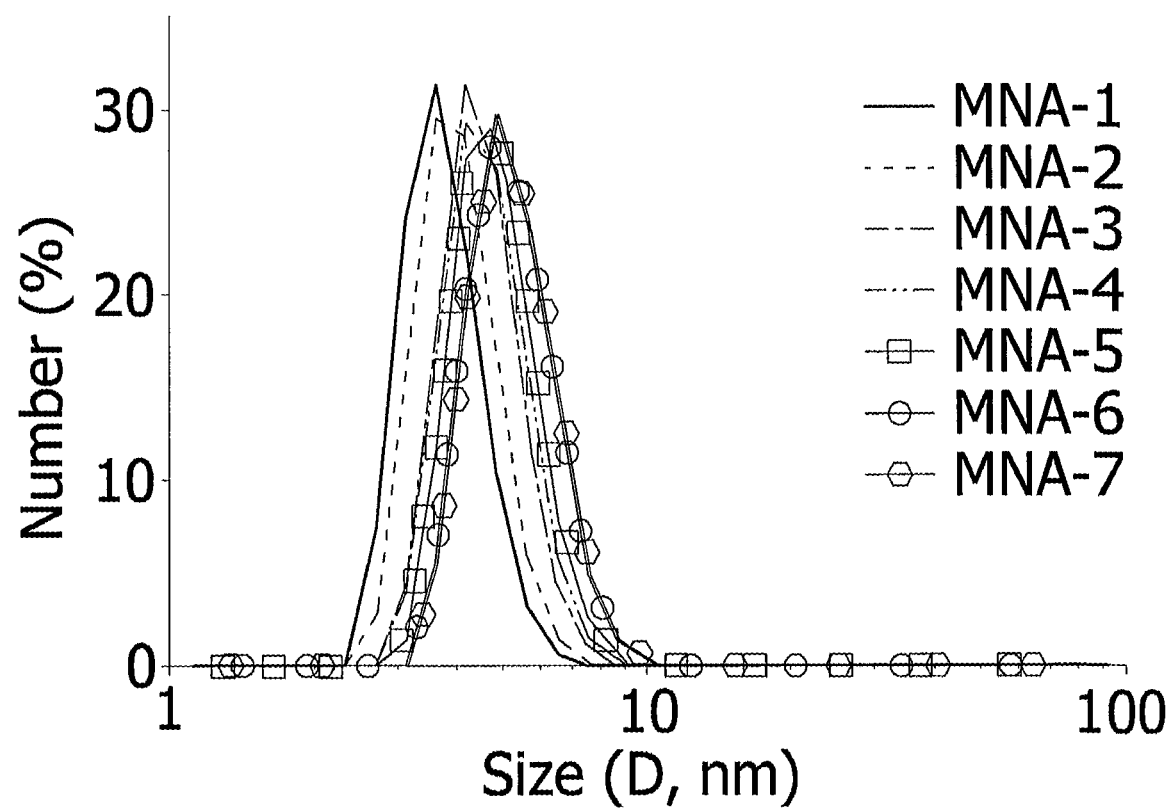

[Figure 18]
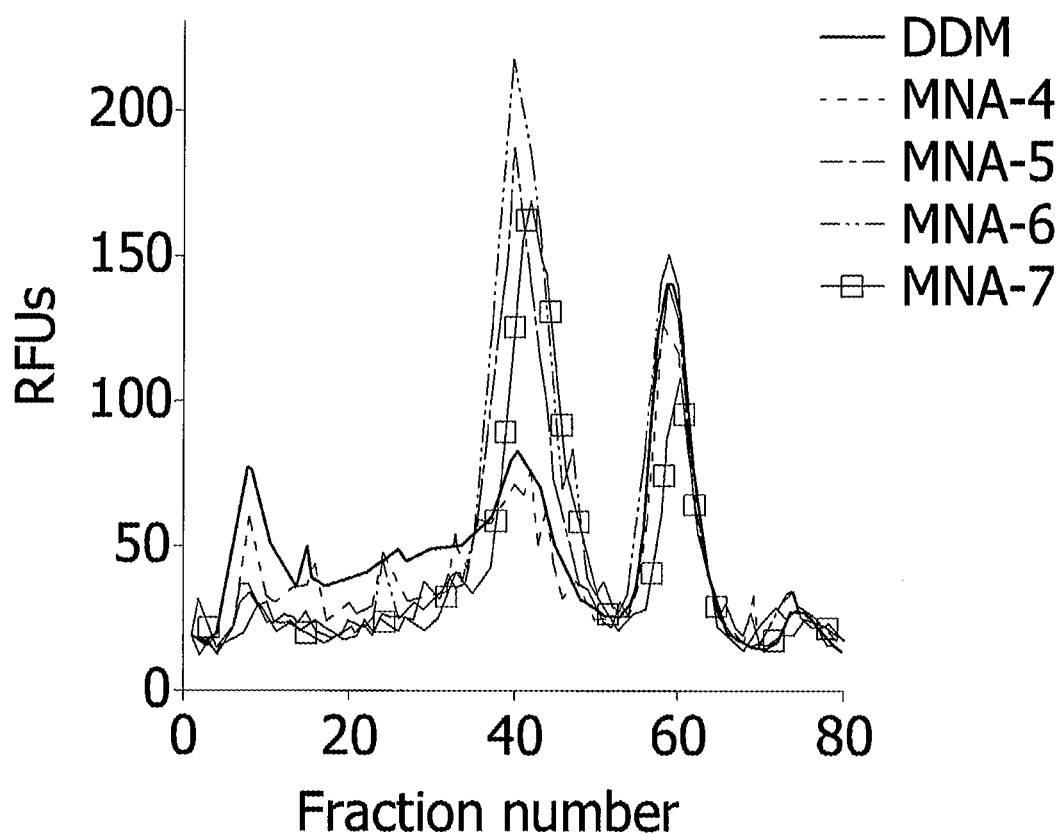

[Figure 19]
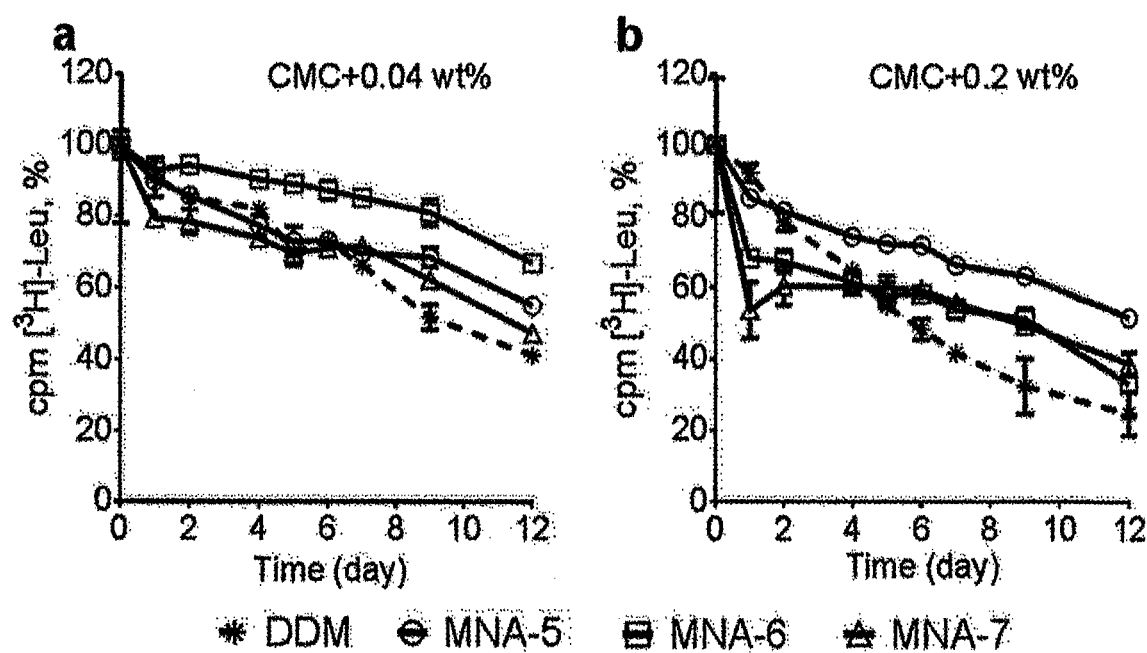

[Figure 20]
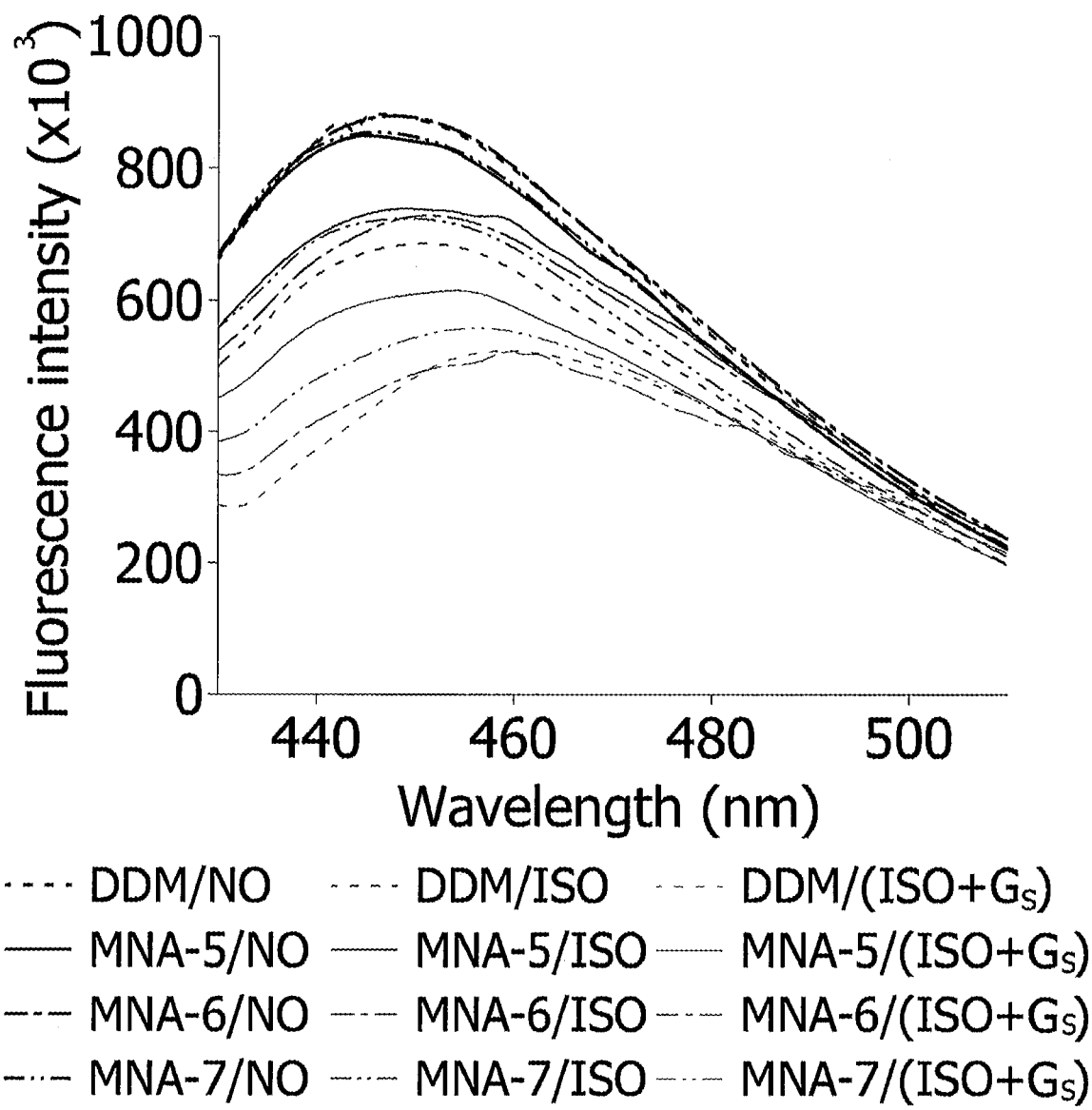

[Figure 21]
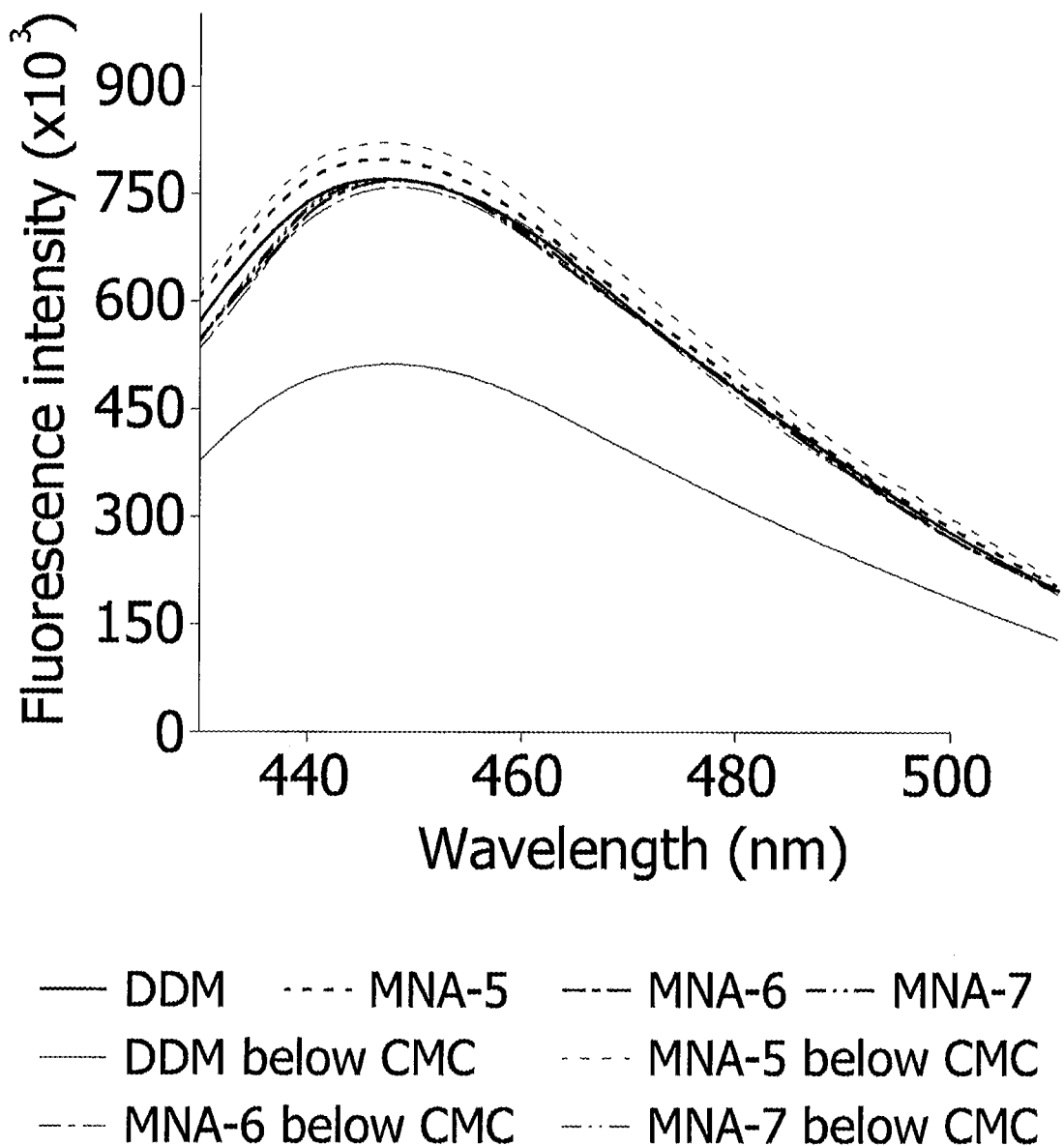

[Figure 22]
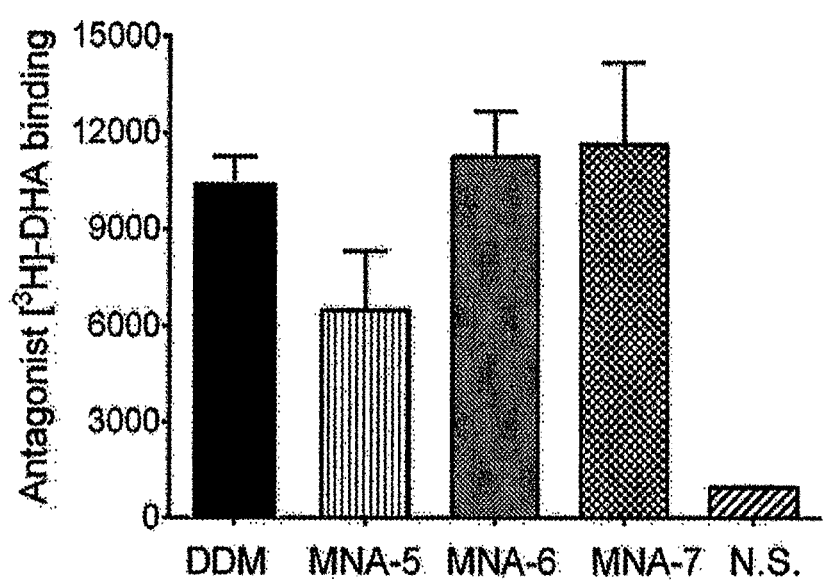

[Figure 23]
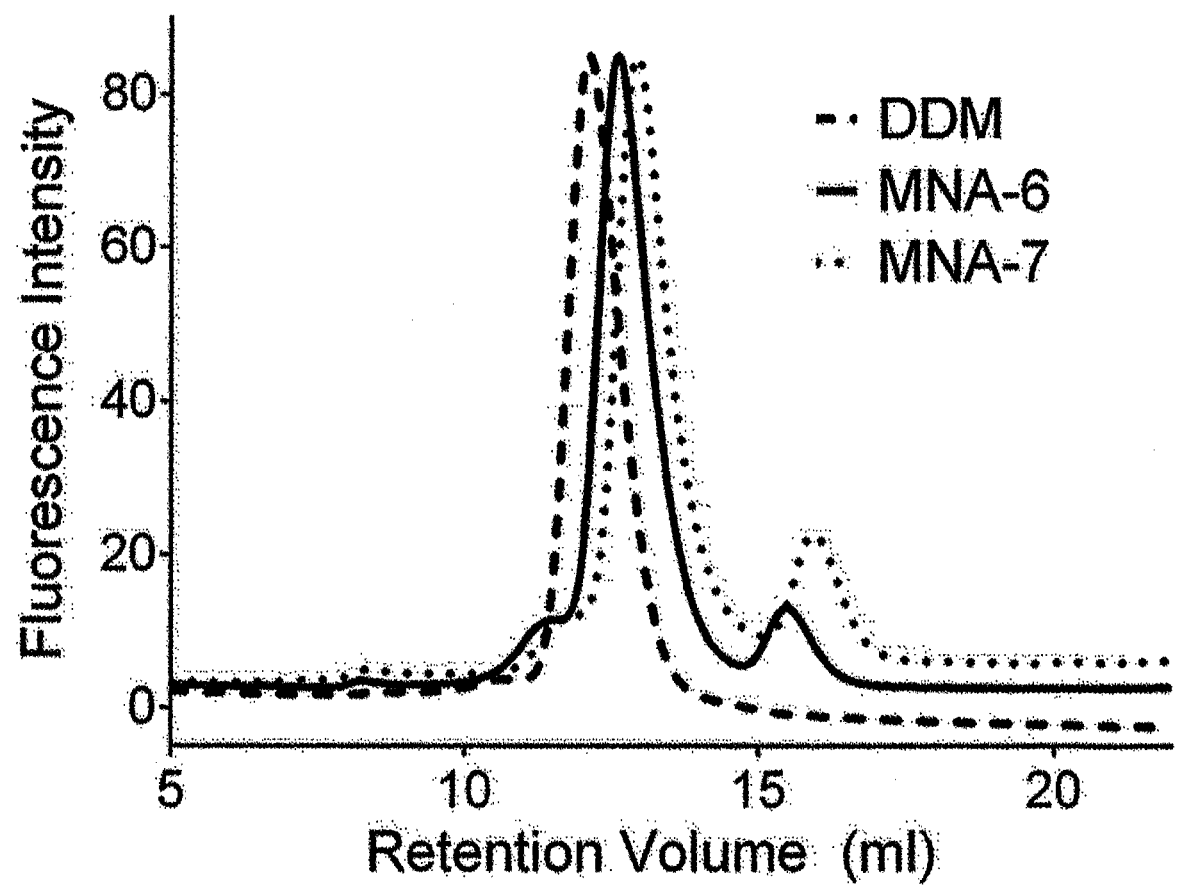

[Figure 24]
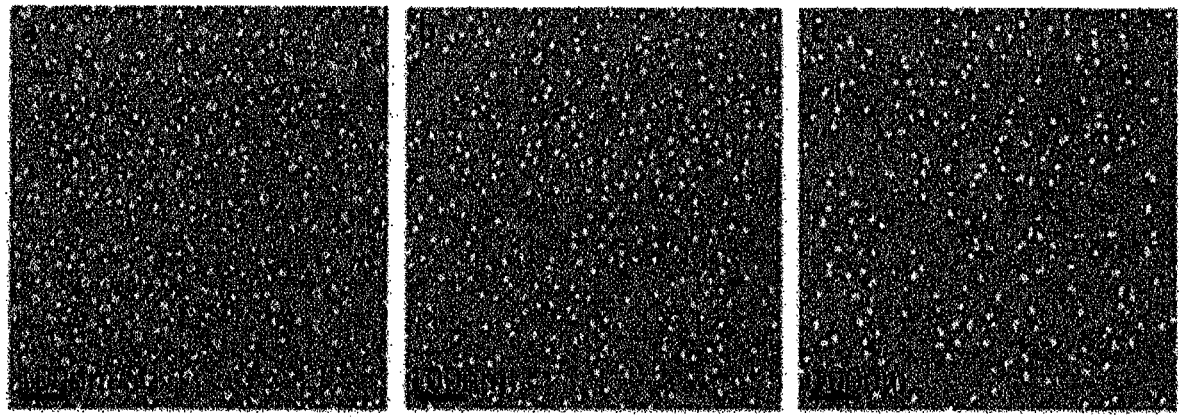

MANNITOL-BASED AMPHIPATHIC COMPOUND AND USE THEREOF

TECHNICAL FIELD

The present invention relates to a newly developed mannitol-based amphipathic compound, a composition for extracting, solubilizing, stabilizing or crystallizing a membrane protein including the compound or a composition for analyzing a structure of the membrane protein using an electron microscope, a method of preparing the compound, a method of extracting, solubilizing, stabilizing or crystallizing a membrane protein using the compound, and a method of analyzing a structure of the membrane protein under an electron microscope using the compound.

BACKGROUND ART

Membrane proteins play important roles in biological systems. Since such bio-macromolecules include hydrophilic and hydrophobic moieties, amphipathic molecules are required to extract membrane proteins from lipid environments and solubilize and stabilize the membrane proteins in an aqueous solution.

High-quality crystals of the membrane proteins should be obtained to analyze the structure of the membrane proteins. For this purpose, the structural stability of the membrane proteins in an aqueous solution should first be ensured. There are a large number of conventional amphipathic molecules (e.g., 100 or more amphipathic number of conventional amphipathic molecules (e.g., 100 or more amphipathic molecules) which are being used to conduct research on membrane proteins. However, approximately 5 of the amphipathic molecules have been most widely used in the structural studies of the membrane proteins. The five amphipathic molecules include n-octyl-β-D-glucopyranoside (OG), n-nonyl-β-D-glucopyranoside (NG), n-decyl-β-D-maltopyranoside (DM), n-dodecyl-β-D-maltopyranoside (DDM), and lauryldimethylamine-N-oxide (LDAO) (see Non-patent Documents 1 and 2). However, since the membrane proteins surrounded by these molecules rapidly lose their functions due to their denaturation or aggregation, there are many limitations in the research of the functions and structures of the membrane proteins using the molecules. This is because the conventional amphipathic molecules do not exhibit a wide variety of characteristics due to their simple chemical structures. Therefore, a development of novel amphipathic materials having new and excellent characteristics through novel structures is needed.

Accordingly, the present inventors have developed novel amphipathic compounds capable of being used in research on membrane proteins. Therefore, the present invention has been completed based on these facts.

(Non-patent Document 1) S. Newstead et al., Protein Sci. 17 (2008) 466-472.

(Non-patent Document 2) S. Newstead et al., Mol. Membr. Biol. 25 (2008) 631-638.

DISCLOSURE

Technical Problem

According to one aspect of the present invention, the present invention is directed to providing a compound represented by Formula 1.

According to another aspect of the present invention, the present invention is directed to providing a composition including the compound for extracting, solubilizing, stabilizing or crystallizing a membrane protein, or for analyzing a structure of the membrane protein using an electron microscope.

According to still another aspect of the present invention, the present invention is directed to providing a method of preparing the compound.

According to yet another aspect of the present invention, the present invention is directed to providing a method of extracting, solubilizing, stabilizing, or crystallizing a membrane protein using the compound.

According to yet another aspect of the present invention, the present invention is directed to providing a method of analyzing a structure of the membrane protein under an electron microscope using the compound.

Technical Solution

To solve the above problems, one aspect of the present invention provides a compound represented by the following Formula 1:

[Formula 1]

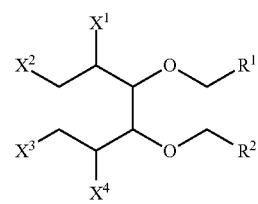

In Formula 1, $R^1$ and $R^2$ may each independently be a substituted or unsubstituted $C_5$-$C_{20}$ alkyl group, a substituted or unsubstituted $C_5$-$C_{20}$ cycloalkyl group, or a substituted or unsubstituted $C_5$-$C_{20}$ aryl group; and $X^1$, $X^2$, $X^3$ and $X^4$ may each independently be an oxygen-linked saccharide.

The term "saccharide" used herein refers to a compound including relatively smaller molecules among carbohydrates and sweet tasting when dissolved in water. Saccharides are divided into monosaccharides, disaccharides, and polysaccharides depending on the number of the molecules constituting the saccharide.

The saccharide used in one aspect of the present invention may be a monosaccharide or a disaccharide, particularly glucose or maltose, and more particularly glucose, but the present invention is not limited thereto.

The saccharide may serve as a hydrophilic group. The compound according to one exemplary embodiment of the present invention has a reduced size of protein-detergent complexes when the compound forms a complex with the membrane protein by having four saccharides as hydrophilic groups bonded in parallel. This molecular architecture will increase the size of the hydrophilic groups yet minimize an increase in length of the hydrophilic groups. When the complex of the compound with the membrane protein is small in size, high-quality crystals of a membrane protein may be obtained (G. G. Prive, *Methods* 2007, 41, 388-397).

Also, $R^1$ and $R^2$ may serve as hydrophobic groups.

Therefore, the compound according to one exemplary embodiment of the present invention may have a structure in which hydrophobic groups and hydrophilic groups are bonded by mannitol linkers.

Specifically, $R^1$ and $R^2$ may be a $C_7$-$C_{18}$ alkyl group; $R^1$ and $R^2$ may be the same; and $X^1$ to $X^4$ may each be an oxygen-linked glucose compound named "mannitol-based amphiphiles (MNAs)."

The compound may be a compound represented by Formula 2, Formula 3, Formula 4, Formula 5, Formula 6, Formula 7, Formula 8, Formula 9, Formula 10, or Formula 11 according to one example of the present invention, but the present invention is not limited thereto.

According to one exemplary embodiment of the present invention, the compound whose $R^1$ and $R^2$ are each a $C_7$ alkyl group and $X^1$ to $X^4$ are each oxygen-linked glucose was named "MNA-1." Therefore, the compound may be a compound represented by the following Formula 2:

[Formula 2]

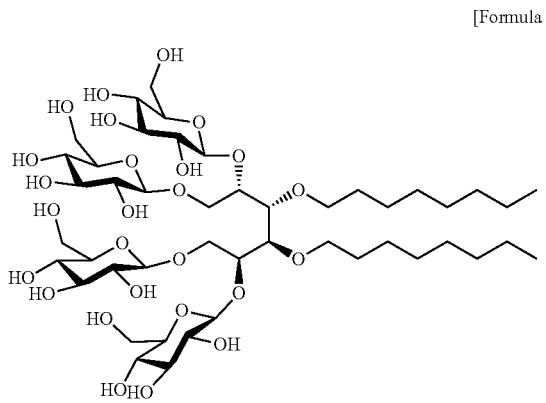

According to another exemplary embodiment of the present invention, the compound whose $R^1$ and $R^2$ are each a $C_8$ alkyl group and $X^1$ to $X^4$ are each oxygen-linked glucose was named "MNA-2." Therefore, the compound may be a compound represented by the following Formula 3:

[Formula 3]

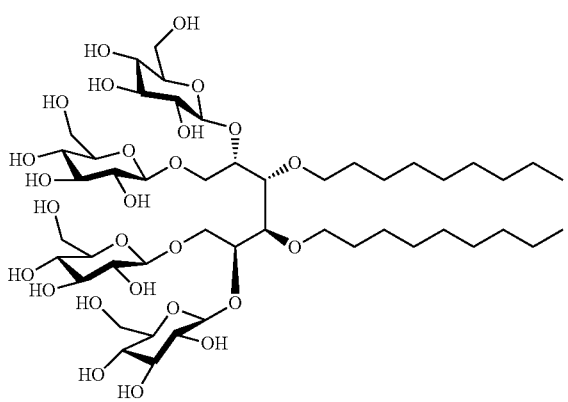

According to still another exemplary embodiment of the present invention, the compound whose $R^1$ and $R^2$ are each a $C_9$ alkyl group and $X^1$ to $X^4$ are each oxygen-linked glucose was named "MNA-3." Therefore, the compound may be a compound represented by the following Formula 4:

[Formula 4]

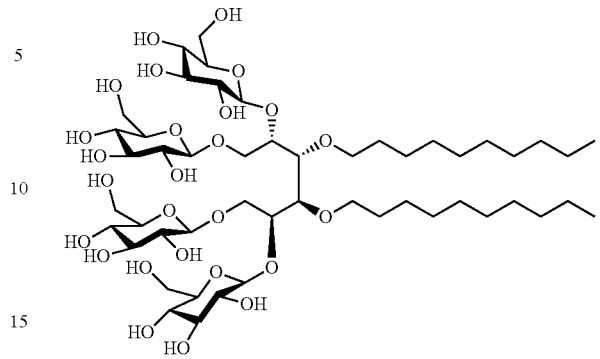

According to yet another exemplary embodiment of the present invention, the compound whose $R^1$ and $R^2$ are each a $C_{10}$ alkyl group and $X^1$ to $X^4$ are each oxygen-linked glucose was named "MNA-4." Therefore, the compound may be a compound represented by the following Formula 5:

[Formula 5]

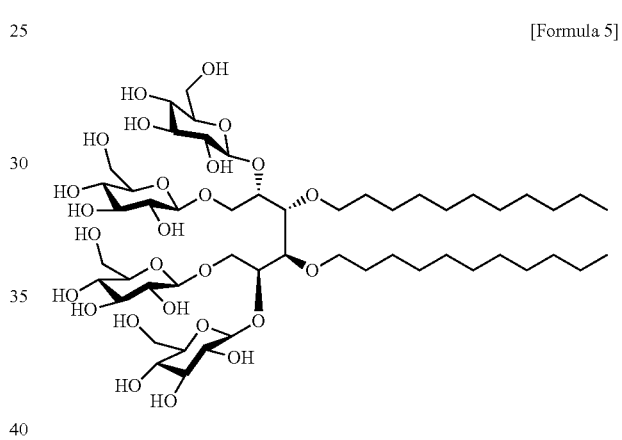

According to yet another exemplary embodiment of the present invention, the compound whose $R^1$ and $R^2$ are each a $C_{11}$ alkyl group and $X^1$ to $X^4$ are each oxygen-linked glucose was named "MNA-5." Therefore, the compound may be a compound represented by the following Formula 6:

[Formula 6]

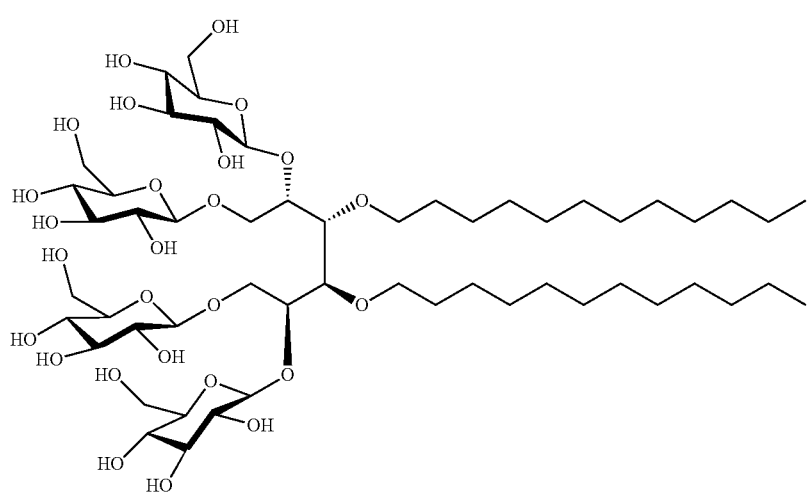

According to yet another exemplary embodiment of the present invention, the compound whose $R^1$ and $R^2$ are each a $C_{12}$ alkyl group and $X^1$ to $X^4$ are each oxygen-linked glucose was named "MNA-6." Therefore, the compound may be a compound represented by the following Formula 7:

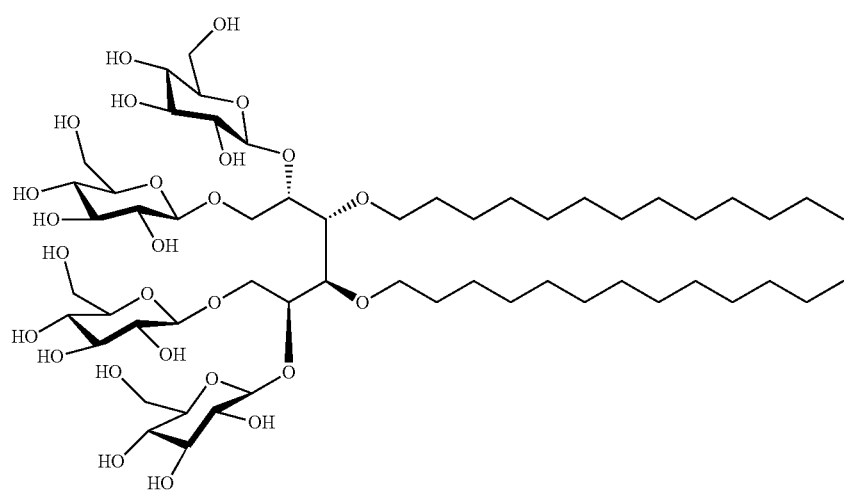

[Formula 7]

According to yet another exemplary embodiment of the present invention, the compound whose $R^1$ and $R^2$ are each a $C_{13}$ alkyl group and $X^1$ to $X^4$ are each oxygen-linked glucose was named "MNA-7." Therefore, the compound may be a compound represented by the following Formula 8:

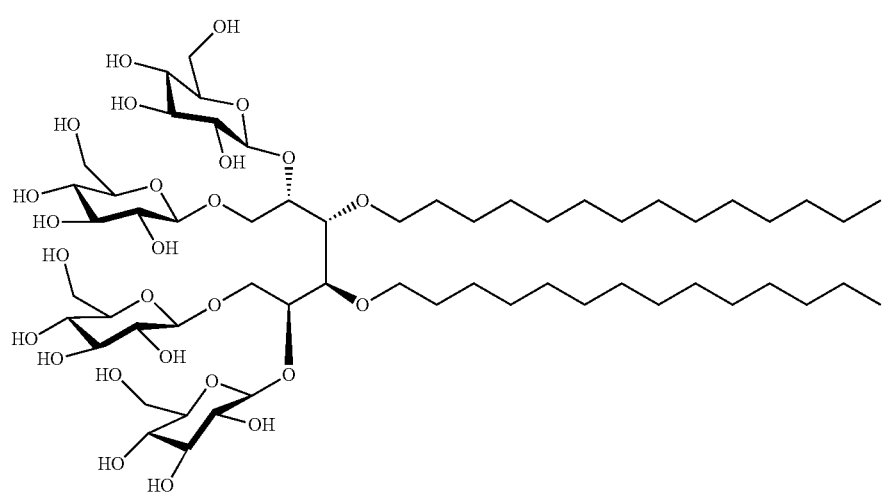

[Formula 8]

According to yet another exemplary embodiment of the present invention, the compound whose $R^1$ and $R^2$ are each a $C_{14}$ alkyl group and $X^1$ to $X^4$ are each oxygen-linked glucose was named "MNA-8." Therefore, the compound may be a compound represented by the following Formula 9:

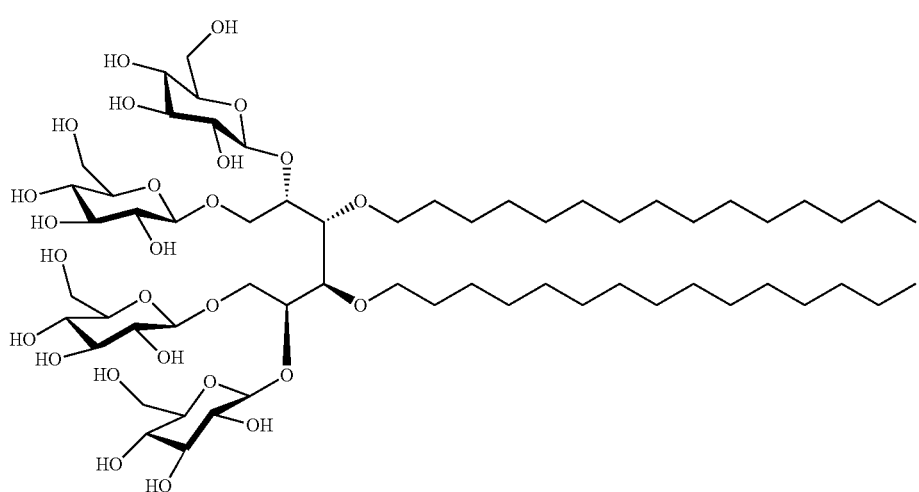

According to yet another exemplary embodiment of the present invention, the compound whose $R^1$ and $R^2$ are each a $C_{15}$ alkyl group and $X^1$ to $X^4$ are each oxygen-linked glucose was named "MNA-9." Therefore, the compound may be a compound represented by the following Formula 10:

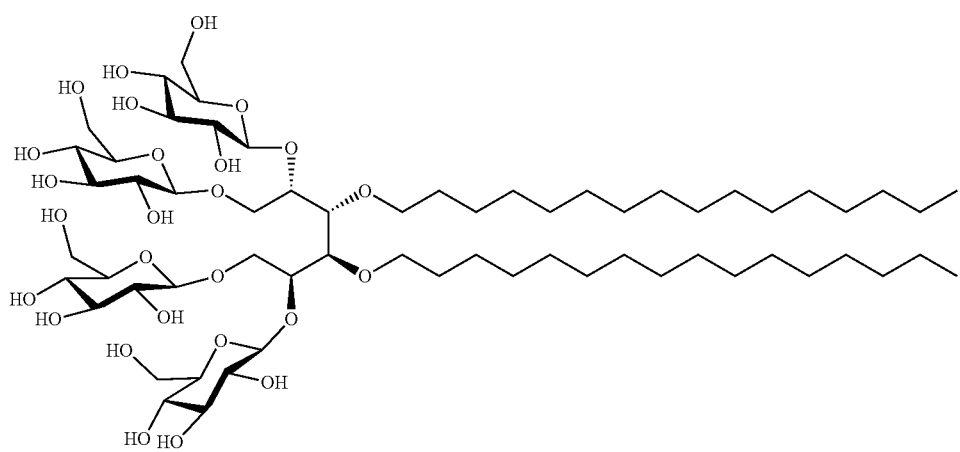

According to yet another exemplary embodiment of the present invention, the compound whose $R^1$ and $R^2$ are each a $C_{16}$ alkyl group and $X^1$ to $X^4$ are each oxygen-linked glucose was named "MNA-10." Therefore, the compound may be a compound represented by the following Formula 11:

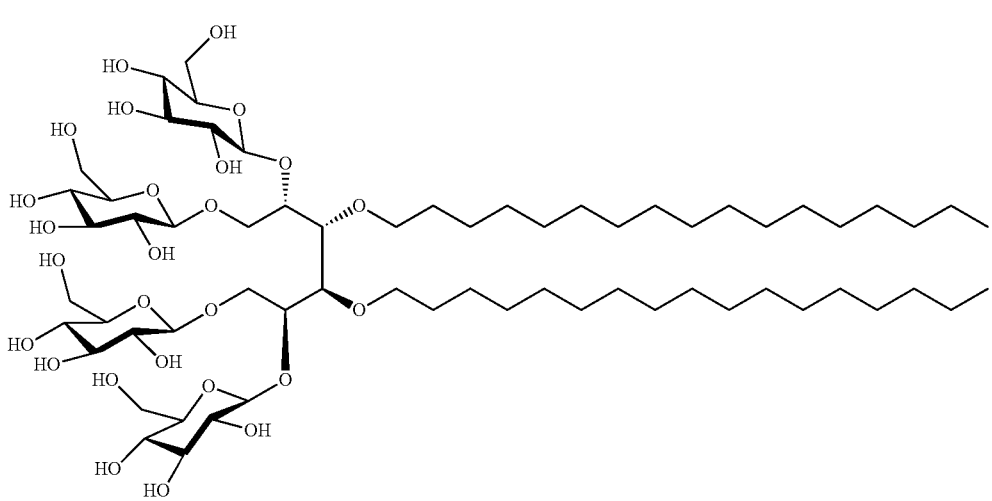

The compound according to another exemplary embodiment of the present invention may be an amphipathic molecule for extracting, solubilizing, stabilizing, or crystallizing the membrane protein, but the present invention is not limited thereto.

The compound according to still another exemplary embodiment of the present invention may be an amphipathic molecule which may form a complex with the membrane protein for analyzing a structure of the membrane protein using an electron microscope, but the present invention is not limited thereto.

The term "amphipathic molecule" used herein refers to a molecule that has both hydrophobic and hydrophilic characteristics in a polar or non-polar solvent due to the presence of both hydrophobic and hydrophilic groups in a single molecule. Detergent molecules or phospholipid molecules present in a cell membrane have a hydrophilic group at one end thereof and a hydrophobic group at the other and thus have a characteristic of forming micelles or liposomes in an aqueous solution due to their amphipathic properties. Even though the detergent molecules have a polar characteristic, because of the coexisting non-polar hydrophobic groups, the amphipathic molecules thereof tend to be insoluble in water. However, when the concentration of the detergent molecules is greater than a characteristic concentration value (critical micellar concentration, CMC), micelles in which the hydrophobic groups are oriented toward the interior and the hydrophilic groups are orientated toward surface are formed via hydrophobic interactions, resulting in an increased solubility in water.

A method of measuring the CMC is not particularly limited, but the methods widely known in the related art may be used. For example, the CMC may be measured by a fluorescence detection method using diphenylhexatriene (DPH).

The compound according to one exemplary embodiment of the present invention may have a critical micellar concentration (CMC) of $1 \times 10^{-4}$ mM to 1.0 mM in an aqueous solution, particularly $1 \times 10^{-4}$ mM or more and less than 0.2 mM, and more particularly $1 \times 10^{-4}$ mM or more and less than 0.17 mM, and most particularly $1 \times 10^{-4}$ mM to 0.16 mM, but the present invention is not limited thereto.

DDM that is widely used in prior research of membrane proteins has a critical micellar concentration of 170 µM. The MNAs according to one aspect of the present invention have a CMC value similar to or smaller than that of the DDM. Therefore, it is possible to confirm that micelles are readily formed even with a small quantity of the MNAs, and thus the MNAs have an advantage over DDM since only a small quantity is required for effectively studying and analyzing the membrane proteins.

Another aspect of the present invention provides a composition for extracting, solubilizing, stabilizing or crystallizing a membrane protein that includes the compound, or a composition for analyzing a structure of the membrane protein using an electron microscope.

The composition may be a micelle, a liposome, an emulsion, or a nanoparticle formulation, but the present invention is not limited thereto.

The micelle may have a radius of 2.0 nm to 4.5 nm, particularly a radius of 2.1 nm to 4.4 nm, but the present invention is not limited thereto.

A method of measuring the radius of the micelle is not particularly limited, but the methods widely known in the related art may be used. For example, the radius of the micelle may be measured using a dynamic light scattering (DLS) experiment.

It can be seen that, since most of the MNAs have a smaller micelle size compared to DDM giving a radius of 3.4 nm, membrane proteins may be more easily separated from the micelles formed by such amphipathic molecules.

The micelle, the liposome, the emulsion or the nanoparticle may have a membrane protein embedded inside. That is, the micelle, the liposome, the emulsion or the nanoparticle formulation may extract and encapsulate the membrane proteins from cell membranes. Therefore, it is possible to extract, solubilize, stabilize, or crystallize the membrane protein using the micelle or to analyze a structure of the membrane protein using an electron microscope.

The composition may further include a buffer which may aid in extracting, solubilizing, or stabilizing the membrane protein, etc.

Still another aspect of the present invention provides a method of preparing a compound represented by the following Formula 1, which includes the following steps 1) to 4):

1) subjecting (1 R,2R)-1,2-bis((S)-2,2-dimethyl-1,3-dioxolan-4-yl)ethane-1,2-diol to an alkylation reaction to introduce two alkyl groups;

2) adding p-toluenesulfonic acid (p-TSA), $CH_2Cl_2$ and methanol to the product of step 1) to produce a 3,4-O-dialkyl-D-mannitol;

3) subjecting the product of step 2) to a glycosylation reaction to introduce two saccharide units to which protecting groups are attached; and 4) subjecting the product of step 3) to a deprotection reaction to remove an O-benzoyl group:

[Formula 1]

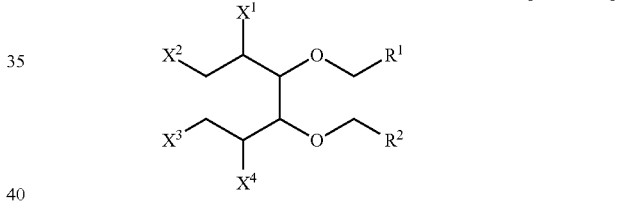

In Formula 1, $R^1$ and $R^2$ may each independently be a substituted or unsubstituted $C_5$-$C_{20}$ alkyl group, a substituted or unsubstituted $C_5$-$C_{20}$ cycloalkyl group, or a substituted or unsubstituted $C_5$-$C_{20}$ aryl group; and $X^1$, $X^2$, $X^3$ and $X^4$ may each independently be an oxygen-linked saccharide.

Specifically, each of $R^1$ and $R^2$ may be a $C_7$-$C_{18}$ alkyl group; $R^1$ and $R^2$ may be the same; and $X^1$ to $X^4$ may each be an oxygen-linked glucose, but the present invention is not limited thereto.

The compound may be a compound represented by Formula 2, Formula 3, Formula 4, Formula 5, Formula 6, Formula 7, Formula 8, Formula 9, Formula 10, or Formula 11 according to one exemplary embodiment of the present invention, but the present invention is not limited thereto.

According to another aspect of the present invention, the compound may be synthesized in a simple way through four synthesis steps with no heat application using mannitol with an attached protecting group as the starting material. Since the compound may be easily synthesized by the preparation method of the present invention, the compound for research of the membrane proteins may be mass-produced.

According to one exemplary embodiment of the present invention, MNA-1 to MNA-10 have been prepared by performing the following steps according to a synthesis scheme shown in FIG. 1:

1) Adding an alkyl bromide, DMF and NaH to (1R,2R)-1,2-bis((S)-2,2-dimethyl-1,3-dioxolan-4-yl)ethane-1,2-diol and subjecting the resulting mixture to an alkylation reaction to obtain a 3,4-O-di-alkyl-1,2:4,5-di-O-isopropylidene-D-mannitol (compound A).

2) Adding p-toluenesulfonic acid (p-TSA), CH$_2$Cl$_2$, and methanol to the compound A to obtain a 3,4-O-di-alkyl-D-mannitol (compound B).

3) Adding perbenzoylated glucosylbromide, AgOTf, 1,2-dimethoxyethane, and CH$_2$Cl$_2$ to the compound B and subjecting the resulting mixture to a glycosylation reaction to obtain compound C with multiple protecting groups.

4) Adding NaOMe and MeOH to the compound C and subjecting the resulting mixture to a deprotection (de-O-benzoylation) reaction to obtain compound D (MNAs).

Still another aspect of the present invention provides a method of extracting, solubilizing, stabilizing, or crystallizing a membrane protein. Specifically, the method may be a method of extracting, solubilizing, stabilizing, or crystallizing a membrane protein which includes a step of treating the membrane protein with the compound represented by the following Formula 1 in an aqueous solution:

[Formula 1]

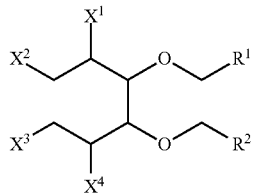

In Formula 1, R$^1$ and R$^2$ may each independently be a substituted or unsubstituted C$_5$-C$_{20}$ alkyl group, a substituted or unsubstituted C$_5$-C$_{20}$ cycloalkyl group, or a substituted or unsubstituted C$_5$-C$_{20}$ aryl group; and X$^1$, X$^2$, X$^3$ and X$^4$ may each independently be an oxygen-linked saccharide.

Specifically, each of R$^1$ and R$^2$ may be a C$_7$-C$_{18}$ alkyl group; R$^1$ and R$^2$ may be the same; and each of X$^1$ to X$^4$ may be an oxygen-linked glucose, but the present invention is not limited thereto.

The compound may be a compound represented by Formula 2, Formula 3, Formula 4, Formula 5, Formula 6, Formula 7, Formula 8, Formula 9, Formula 10, or Formula 11 according to one exemplary embodiment of the present invention, but the present invention is not limited thereto.

The term "membrane protein" used herein generally refers to a protein or a glucoprotein introduced into a lipid bilayer of a cell membrane. The membrane protein is present in various manners, for example, penetrating across an entire layer of the cell membrane, existing on a surface layer of the cell membrane, or lining the cell membranes, etc. Examples of the membrane proteins may include receptors such as enzymes, peptide hormones, and local hormones, acceptor carriers such as sugars, ion channels, cell membrane antigens, etc., but the present invention is not limited thereto.

The membrane protein may include any proteins or glycoproteins as long as the proteins or glycoproteins are introduced into a lipid bilayer of a cell membrane. Specifically, the membrane protein may be a boron transporter (Bor1), a leucine transporter (LeuT), a human β$_2$ adrenergic receptor (β$_2$AR), a ATP-binding cassette (ABC) transporter, or a combination of two or more thereof, but the present invention is not limited thereto.

The term "extraction of membrane proteins" used herein refers to separating membrane proteins from cell membranes.

The term "solubilization of membrane proteins" used herein refers to dissolving membrane proteins which are insoluble in water into micelles in an aqueous solution.

The term "stabilization of membrane proteins" used herein refers to stably preserving native structures of the membrane proteins to prevent changes in structures and functions of the membrane proteins.

The term "crystallization of membrane proteins" used herein refers to forming crystals of the membrane proteins in a solution.

Yet another aspect of the present invention provides a method of analyzing a structure of the membrane protein using an electron microscope. Specifically, the method may be a method of analyzing a structure of the membrane protein using an electron microscope including the following steps 1) to 3):

1) treating the membrane protein with a compound represented by the following Formula 1 in an aqueous solution;

2) staining the membrane protein dissolved by the compound; and 3) analyzing the stained membrane protein using the electron microscope:

[Formula 1]

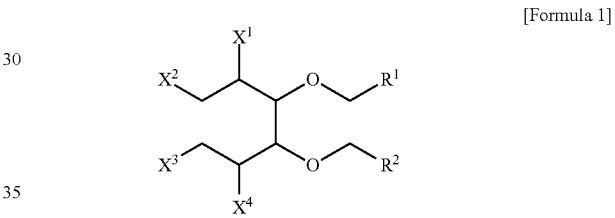

In Formula 1, R$^1$ and R$^2$ may each independently be a substituted or unsubstituted C$_5$-C$_{20}$ alkyl group, a substituted or unsubstituted C$_5$-C$_{20}$ cycloalkyl group, or a substituted or unsubstituted C$_5$-C$_{20}$ aryl group; and X$^1$, X$^2$, X$^3$ and X$^4$ may each independently be an oxygen-linked saccharide.

Specifically, each of R$^1$ and R$^2$ may be a C$_7$-C$_{18}$ alkyl group; R$^1$ and R$^2$ may be the same; and each of X$^1$ to X$^4$ may be an oxygen-linked glucose, but the present invention is not limited thereto.

The compound of step 1) may be a compound represented by Formula 2, Formula 3, Formula 4, Formula 5, Formula 6, Formula 7, Formula 8, Formula 9, Formula 10, or Formula 11 according to one exemplary embodiment of the present invention, but the present invention is not limited thereto.

The membrane protein may be a boron transporter (Bor1), a leucine transporter (LeuT), a human β$_2$ adrenergic receptor (β$_2$AR), an ATB-binding cassette (ABC) transporter, or a combination of two or more thereof, but the present invention is not limited thereto.

A membrane protein-compound complex (a protein-detergent complex) may be formed in step 1), but the present invention is not limited thereto.

The staining of step 2) may be performed using known methods for staining to enable an electron microscopic analysis of the membrane protein. According to one exemplary embodiment of the present invention, the membrane protein dissolved by the amphipathic molecules has been pipetted onto a glow-discharged carbon-coated grid, and then stained with uranyl formate (M. Ohi et al., *Biol. Proced.*

Online 2004, 6, 23-34.), but the present invention is not limited to such exemplary embodiments.

The analysis of step 3) refers to analyzing a structure of the membrane protein using an electron microscope and may be performed using known methods.

The term "analysis of a structure of a membrane protein using an electron microscope" used herein refers to determining and analyzing the structure of the membrane protein using an electron microscope.

Advantageous Effects

When the mannitol-based compounds according to the exemplary embodiments of the present invention are used, the membrane protein can be stably stored in an aqueous solution for a prolonged period of time compared to conventional compounds and thus can be applied to an analysis of functions and structures thereof.

Since the analysis of the structures and functions of the membrane protein is one of the fields of most interest in biology and chemistry currently and more than half of new drugs currently in development are targeting membrane proteins, the present invention is applicable to research on the structures of proteins closely related to the development of the new drugs.

Specifically, because the complex of the membrane protein and a compound according to the exemplary embodiments of the present invention is small and can improve stability of the membrane protein, a high-resolution structural analysis of the membrane protein through crystallization is possible, and a conformational analysis of the membrane protein using an electron microscope is well suited.

Also, the compounds according to the exemplary embodiments of the present invention can be synthesized from readily available starting materials using simple methods, making it possible to mass-produce the compounds used to study the membrane proteins.

DESCRIPTION OF DRAWINGS

FIG. 1 is a diagram showing a synthesis scheme for MNAs according to Example 1 of the present invention.

FIG. 2 is a diagram showing chemical structures of MNAs according to exemplary embodiments of the present invention.

FIG. 3 is a diagram showing the $^1$H NMR spectrum of MNA-1.

FIG. 4 is a diagram showing the $^{13}$C NMR spectrum of MNA-1.

FIG. 5 is a diagram showing the $^1$H NMR spectrum of MNA-2.

FIG. 6 is a diagram showing the $^{13}$C NMR spectrum of MNA-2.

FIG. 7 is a diagram showing the $^1$H NMR spectrum of MNA-3.

FIG. 8 is a diagram showing the $^{13}$C NMR spectrum of MNA-3.

FIG. 9 is a diagram showing the $^1$H NMR spectrum of MNA-4.

FIG. 10 is a diagram showing the $^{13}$C NMR spectrum of MNA-4.

FIG. 11 is a diagram showing the $^1$H NMR spectrum of MNA-5.

FIG. 12 is a diagram showing the $^{13}$C NMR spectrum of MNA-5.

FIG. 13 is a diagram showing the $^1$H NMR spectrum of MNA-6.

FIG. 14 is a diagram showing the $^{13}$C NMR spectrum of MNA-6.

FIG. 15 is a diagram showing the $^1$H NMR spectrum of MNA-7.

FIG. 16 is a diagram showing the $^{13}$C NMR spectrum of MNA-7.

FIG. 17 is a diagram showing a size (diameter (D), nm) distribution of micelles formed by the MNAs.

FIG. 18 is a diagram showing the results obtained by measuring structural stability of a boron transporter (Bor1) in CMC plus 0.04% by weight of MNAs (MNA-4, MNA-5, MNA-6, or MNA-7) or DDM using heat fluorescence size exclusion chromatography (hFSEC).

FIG. 19 is a diagram showing the results obtained by measuring structural stability of a leucine transporter (LeuT) in MNAs (MNA-5, MNA-6, or MNA-7) or DDM using a scintillation proximity assay (SPA):
(a) [$^3$H]-Leucine binding ratios (%) when CMC plus 0.04% by weight of MNAs (MNA-5, MNA-6, or MNA-7) or DDM is used; and
(b) [$^3$H]-Leu binding ratios (%) when CMC plus 0.2% by weight of MNAs (MNA-5, MNA-6, or MNA-7) or DDM is used.

FIG. 20 is a diagram showing the fluorescence spectra of mBBr-$\beta_2$AR dissolved in MNAs (MNA-5, MNA-6, or MNA-7) or DDM according to the presence or absence of a full agonist (isopreoterenol (ISO)) or a combination of ISO and G-protein.

FIG. 21 is a diagram showing changes in the fluorescence spectra of mBBr-$\beta_2$AR when the concentration of MNAs (MNA-5, MNA-6, or MNA-7) or DDM is reduced to one fiftieth of their CMCs.

FIG. 22 is a diagram showing the results obtained by measuring ligand ([$^3$H]-DHA) binding activity of $\beta_2$AR dissolved in MNAs (MNA-5, MNA-6, or MNA-7) or DDM.

FIG. 23 is a diagram showing the size exclusion chromatography (SEC) analysis results to determine the sizes of $\beta_2$AR-amphipathic molecule complexes (PDCs) formed by MNA (MNA-6 or MNA-7) or DDM. FIG. 24 is a diagram showing the electron microscopy (EM) results of analysis of $\beta_2$AR dissolved by DDM (A), MNA-6 (B), or MNA-7 (C).

BEST MODE

Hereinafter, the present invention will be described in further detail with reference to exemplary embodiments thereof. However, it should be understood that the description proposed herein is just a preferable example for the purpose of illustrations only, not intended to limit or define the scope of the invention. Accordingly, it will be apparent to those skilled in the art that various changes and modifications can be made to the exemplary embodiments of the present invention without departing from the scope of the present invention, so it should be understood that the present invention covers all such changes and modifications provided they are within the scope of the appended claims and their equivalents.

<Example 1>

Synthesis Method of Mannitol-Based Amphiphiles (MNAs)

A synthesis scheme of MNAs is shown in FIG. 1. Ten mannitol-based amphiphiles (MNAs) were synthesized according to synthesis methods of Examples <1-1> to <1-4> below and are shown in FIG. 2.

<1-1>General Synthesis Procedure for Synthesis of 3,4-O-di-alkyl-1,2:4,5-di-O-isopropylidene-D-mannitol (Step a; Synthesis of Compound A)

Compound A was synthesized using mannitol to which a protecting group was introduced (protected mannitol) as a starting material.
Specifically, a starting material, (1R,2R)-1,2-bis((S)-2,2-dimethyl-1,3-dioxolan-4-yl)ethane-1,2-diol, was added to a cold suspension of dissolved sodium hydride (3 equivalents) in anhydrous DMF and stirred for 30 minutes. Thereafter, an alkyl bromide (2.2 equivalents) was added, and the resulting reaction mixture was stirred at room temperature for 4 hours. Sodium hydride remaining after the reaction was quenched using a few drops of methanol, and an organic compound was extracted with $CH_2Cl_2$ and washed with distilled water (3×20 mL). The collected organic layer was dried over anhydrous $Na_2SO_4$ and evaporated by a rotary evaporator. The product was purified using silica gel column chromatography to obtain a pure 3,4-O-di-alkyl-1,2:4,5-di-O-isopropylidene-D-mannitol (compound A).

<1-2>General Synthesis Procedure for Synthesis of 3,4-O-di-alkyl-D-mannitol (Step b; A→B)

The compound A synthesized in Example 1-1 was added to a stirring solution of methanol (25 mL) and $CH_2Cl_2$ (25 mL) (1:1) with 200 mg of p-TSA and stirred overnight at room temperature. After the reaction was completed, solid $NaHCO_3$ was slowly added and vigorously stirred to neutralize the reaction mixture. The reaction mixture was filtered and dried using a rotary evaporator, and the resulting product was purified by silica gel column chromatography (EtOAc/hexane) to obtain a 3,4-O-di-alkyl-D-mannitol (compound B).

<1-3>General Synthesis Procedure for Glycosylation Reaction (Step c; B→C)

Glycosylation was carried out according to a modified method defined in the article by P. S. Chae et al. (*Nat. Methods* 2010, 7. 1003-1008.). Specifically, the alcohol derivative (compound B) synthesized in Example 1-2 was dissolved in $CH_2Cl_2$ (15 mL) at room temperature, and molecular sieves (4 Å) were added thereto. AgOTf (6.9 equivalents) was added to the mixture at 0° C., and a perbenzoylated glucosylbromide solution (6.8 equivalents) dissolved in $CH_2Cl_2$ (2 mL) was slowly added. After 15 minutes of the reaction at 0° C., the reaction mixture was warmed to room temperature and then stirred for an hour. After the reaction was completed (confirmed by TLC analysis), pyridine was added to stop the reaction. Then, the mixture was diluted with $CH_2Cl_2$ (20 mL), and filtered through celite. The resulting filtrate was successively washed with a 1 M $Na_2S_2O_3$ aqueous solution (40 mL), a 0.1 M HCl aqueous solution (40 mL), and brine (3×40 mL). The organic layer was dried on anhydrous $Na_2SO_4$, and a solvent was removed using a rotary evaporator. The residue was purified using silica gel chromatography (EtOAc/hexane) to obtain compound C in a glassy solid state.

<1-4>General Synthesis Procedure for de-O-Benzoylation Under Zemplen's Conditions (Step d; C→D)

The O-benzoylated compound C synthesized in Example 1-3 was dissolved in a small amount of anhydrous $CH_2Cl_2$, and MeOH was added dropwise until precipitation occurred faintly. A required amount of a methanolic solution of 0.5 M NaOMe was slowly added so that the final concentration of NaOMe was 0.05 M. During this, methanol was added at regular intervals to prevent occurrence of precipitates. The reaction mixture was stirred at room temperature for 6 hours and then neutralized with an Amberlite IR-120 ($H^+$ form) resin. The resin was removed by filtration and then washed with MeOH, and a solvent was removed in vacuo from the mixed filtrate. The residual product was purified using silica gel column chromatography. After an additional purification, the residue was recrystallized with $CH_2Cl_2$/MeOH/ diethyl ether to obtain a de-O-benzoylated product (compound D) as a white solid. The compound D obtained thus was named MNAs.

<Preparative Example 1>Synthesis of MNA-1

<1-1>Synthesis of 3,4-O-di-octyl-1,2:5,6-di-O-isopropylidene-D-mannitol (Compound 1)

3,4-O-di-octyl-1,2:5,6-di-O-isopropylidene-D-mannitol (compound 1) was synthesized with a yield of 90% according to the method of Example 1-1 using (1R,2R)-1,2-bis ((S)-2,2-dimethyl-1,3-dioxolan-4-yl)ethane-1,2-diol as a starting material and octyl bromide as an alkyl bromide. The $^1H$ NMR spectra of the separated product were identical to the data reported in the article by J. Walton et al. (*Tetrahedron Lett.* 2006, 47, 737-741.).

<1-2>Synthesis of 3,4-O-di-octyl-D-mannitol (Compound 11)

3,4-O-di-octyl-D-mannitol (compound 11) was synthesized from the compound 1 with a yield of 93% according to the method of Example 1-2. The $^1H$ NMR spectra of the separated product were identical to the data reported in the article by J. Walton et al. (*Tetrahedron Lett.* 2006, 47, 737-741.).

<1-3>Synthesis of MNA-1a

A glycosylation reaction was performed according to the method of Example 1-3 to synthesize MNA-1a from the compound 11 with a yield of 75%. $^1H$ NMR (400 MHz, $CDCl_3$): δ 8.24-8.21 (m, 4H), 8.12-7.98 (m, 4H), 7.97-7.92 (m, 8H), 7.91-7.89 (m, 6H), 7.87-7.79 (m, 16H), 7.61-7.56 (m, 6H), 7.55-7.43 (m, 16H), 7.41-7.35 (m, 32H), 7.34-7.27 (m, 4H), 5.77-5.74 (m, 2H), 5.57-5.42 (m, 4H), 5.41-5.30 (m, 6H), 4.88-4.74 (m, 2H), 4.48-4.46 (m, 2H), 4.45-4.39 (m, 6H), 4.33-4.20 (m, 6H), 4.01-3.91 (m, 2H), 3.54-3.41 (m, 5H), 3.40-3.32 (m, 2H), 3.31-3.14 (m, 4H), 1.81-1.68 (m, 2H), 1.24-1.12 (m, 20H), 0.86 (t, J=7.6 Hz, 6H); $^{13}C$ NMR (100 MHz, $CDCl_3$): δ 165.9, 165.8, 165.6, 165.1, 165.0, 164.8, 133.6, 133.4, 130.0, 129.9, 129.8, 129.7, 129.5, 129.2, 128.9, 128.5, 128.4, 128.3, 101.4, 100.3, 82.4, 73.3, 72.9, 72.8, 72.7, 72.3, 71.8, 71.6, 71.1, 69.9, 69.7, 63.1, 62.9, 32.0, 30.2, 29.6, 29.5, 26.1, 22.8, 14.2.

<1-4>Synthesis of MNA-1

A de-O-benzoylation reaction was performed according to the method of Example 1-4 to synthesize MNA-1, from which a protecting group was removed, from the compound MNA-1a with a yield of 95%. $^1H$ NMR (400 MHz, $CD_3OD$): δ 4.55-4.53 (m, 2H), 4.31-4.30 (m, 2H), 4.13-4.11 (m, 2H), 4.00-3.97 (m, 4H), 3.79-3.72 (m, 4H), 3.70-3.64

(m, 3H), 3.63-3.56 (m, 10H), 3.30-3.21 (m, 15H), 3.20-3.10 (m, 5H), 1.47-1.43 (m, 4H), 1.21 (m, 20H), 0.90 (t, J=8.0 Hz, 6H); $^{13}$C NMR (100 MHz, CD$_3$OD): δ 105.1, 104.7, 82.5, 80.9, 78.2, 78.0, 77.8, 75.6, 75.3, 74.4, 71.6, 71.4, 71.2, 62.8, 62.6, 33.1, 31.4, 30.8, 30.6, 27.4, 23.8, 14.5; HRMS (EI): calculated for C$_{46}$H$_{86}$O$_{26}$[M+Na]$^+$ 1054.5407, found 1054.5406. The $^1$H NMR spectrum of MNA-1 is shown in FIG. 3, and the $^{13}$C NMR spectrum of MNA-1 is shown in FIG. 4.

<Preparative Example 2>Synthesis of MNA-2

<2-1>Synthesis of 3,4-O-di-nonyl-1,2:5,6-di-O-isopropylidene-D-mannitol (Compound 2)

3,4-O-di-nonyl-1,2:5,6-di-O-isopropylidene-D-mannitol (compound 2) was synthesized with a yield of 90% according to the method of Example 1-1 using (1R,2R)-1,2-bis((S)-2,2-dimethyl-1,3-dioxolan-4-yl)ethane-1,2-diol as a starting material and nonyl bromide as an alkyl bromide. The $^1$H NMR spectra of the separated product were identical to the data reported in the article by J. Walton et al. (*Colloids surf A* 2011, 377, 349-355.).

<2-2>Synthesis of 3,4-O-di-nonyl-D-mannitol (Compound 12)

3,4-O-di-octyl-d-mannitol (compound 12) was synthesized from the compound 2 with a yield of 93% according to the method of Example 1-2. The $^1$H NMR spectra of the separated product were identical to the data reported in the article by J. Walton et al. (*Tetrahedron Lett.* 2006, 47, 737-741.).

<2-3>Synthesis of MNA-2a

A glycosylation reaction was performed according to the method of Example 1-3 to synthesize MNA-2a from the compound 12 with a yield of 74%. $^1$H NMR (400 MHz, CDCl$_3$): δ 8.23-8.20 (m, 4H), 8.09-8.01 (m, 4H), 8.00-7.97 (m, 8H), 7.90-7.79 (m, 6H), 7.72-7.65 (m, 16H), 7.61-7.56 (m, 6H), 7.55-7.43 (m, 16H), 7.40-7.35 (m, 32H), 7.34-7.27 (m, 4H), 5.82-5.74 (m, 2H), 5.61-5.51 (m, 4H), 5.49-5.33 (m, 6H), 4.88-4.74 (m, 2H), 4.48-4.46 (m, 2H), 4.45-4.39 (m, 6H), 4.33-4.20 (m, 6H), 4.09-3.95 (m, 2H), 3.58-3.45 (m, 5H), 3.42-3.34 (m, 2H), 3.29-3.19 (m, 4H), 1.83-1.74 (m, 2H), 1.45-1.12 (m, 24H), 0.86 (t, J=7.6 Hz, 6H); $^{13}$C NMR (100 MHz, CDCl$_3$): δ 165.8, 165.3, 165.2, 165.0, 133.8, 133.6, 133.4, 133.2, 130.2, 130.0, 129.8, 129.7, 129.6, 129.4, 129.3, 129.2, 129.1, 128.6, 128.5, 101.5, 100.4, 82.5, 80.2, 73.4, 73.0, 72.9, 72.8, 72.4, 72.2, 72.0, 71.7, 71.2, 70.0, 69.9, 63.3, 63.1, 32.2, 30.3, 29.9, 29.8, 29.6, 26.3, 22.9.

<2-4>Synthesis of MNA-2

A de-O-benzoylation reaction was performed according to the method of Example 1-4 to synthesize MNA-2, from which a protecting group was removed, from the compound MNA-2 with a yield of 94%. $^1$H NMR (400 MHz, CD$_3$OD): δ 4.52-4.51 (m, 2H), 4.29-4.27 (m, 2H), 4.12-4.09 (m, 2H), 3.96-3.94 (m, 4H), 3.80-3.73 (m, 4H), 3.71-3.64 (m, 3H), 3.63-3.53 (m, 10H), 3.27-3.19 (m, 15H), 3.18-3.07 (m, 5H), 1.44-1.39 (m, 4H), 1.19 (m, 24H), 0.90 (t, J=8.0 Hz, 6H); $^{13}$C NMR (100 MHz, CD$_3$OD): δ 105.2, 104.8, 82.6, 81.0, 78.3, 78.1, 77.9, 75.7, 75.4, 74.5, 71.7, 71.5, 71.3, 62.8, 62.7, 33.2, 31.6, 31.0, 30.9 30.6, 27.5, 23.9, 14.6; HRMS (EI): calculated for C$_{48}$H$_{90}$O$_{26}$[M+Na]$^+$ 1082.5720, found 1082.5717. The $^1$H NMR spectrum of MNA-2 is shown in FIG. 5, and the $^{13}$C NMR spectrum of MNA-2 is shown in FIG. 6.

<Preparative Example 3>Synthesis of MNA-3

<3-1>Synthesis of 3,4-O-di-decyl-1,2:5,6-di-O-isopropylidene-D-mannitol (Compound 3)

3,4-O-di-decyl-1,2:5,6-di-O-isopropylidene-D-mannitol (compound 3) was synthesized with a yield of 90% according to the method of Example 1-1 using (1R,2R)-1,2-bis((S)-2,2-dimethyl-1,3-dioxolan-4-yl)ethane-1,2-diol as a starting material and decyl bromide as an alkyl bromide. The $^1$H NMR spectra of the separated product were identical to the data reported in the article by J. Walton et al. (*Tetrahedron Lett.* 2006, 47, 737-741.).

<3-2>Synthesis of 3,4-O-di-decyl-D-mannitol (compound 13)

3,4-O-di-decyl-D-mannitol (compound 13) was synthesized from the compound 3 with a yield of 92% according to the method of Example 1-2. The $^1$H NMR spectra of the separated product were identical to the data reported in the article by J. Walton et al. (*Tetrahedron Lett.* 2006, 47, 737-741.).

<3-3>Synthesis of MNA-3a

A glycosylation reaction was performed according to the method of Example 1-3 to synthesize MNA-3a from the compound 13 with a yield of 71%. $^1$H NMR (400 MHz, CDCl$_3$): δ 8.23-8.20 (m, 4H), 8.12-7.98 (m, 4H), 7.97-7.92 (m, 8H), 7.91-7.89 (m, 6H), 7.87-7.79 (m, 16H), 7.61-7.56 (m, 6H), 7.55-7.43 (m, 16H), 7.40-7.35 (m, 32H), 7.34-7.26 (m, 4H), 5.77-5.74 (m, 2H), 5.57-5.42 (m, 4H), 5.41-5.30 (m, 6H), 4.88-4.74 (m, 2H), 4.48-4.46 (m, 2H), 4.45-4.39 (m, 6H), 4.33-4.20 (m, 6H), 4.01-3.91 (m, 2H), 3.54-3.41 (m, 5H), 3.40-3.32 (m, 2H), 3.31-3.14 (m, 4H), 1.81-1.68 (m, 2H), 1.24-1.12 (m, 28H), 0.86 (t, J=7.6 Hz, 6H); $^{13}$C NMR (100 MHz, CDCl$_3$): δ 166.1, 166.0, 165.8, 165.3 165.2, 165.0, 133.8, 133.6, 133.5133.4, 133.2, 130.2, 130.1, 130.0, 129.9, 129.8, 129.7, 129.6, 129.4, 129.3, 129.2, 129.1, 128.6, 128.5, 101.5, 100.4, 82.4, 73.4, 73.0, 72.8, 72.4, 72.0, 71.8, 71.2, 70.0, 69.9, 63.3, 63.1, 32.2, 30.3, 29.9, 29.7, 26.3, 22.9, 14.3.

<3-4>Synthesis of MNA-3

A de-O-benzoylation reaction was performed according to the method of Example 1-4 to synthesize MNA-3, from which a protecting group was removed, from the compound MNA-3a with a yield of 94%. $^1$H NMR (400 MHz, CD$_3$OD): 6 4.52-4.51 (m, 2H), 4.29-4.27 (m, 2H), 4.12-4.09 (m, 2H), 3.96-3.94 (m, 4H), 3.80-3.73 (m, 4H), 3.71-3.64 (m, 3H), 3.63-3.53 (m, 10H), 3.27-3.19 (m, 15H), 3.18-3.07 (m, 5H), 1.43-1.38 (m, 4H), 1.19 (m, 28H), 0.90 (t, J=8.0 Hz, 6H); $^{13}$C NMR (100 MHz, CD$_3$OD): δ 105.2, 104.8, 82.6, 81.0, 78.3, 78.1, 77.9, 75.7, 75.4, 74.5, 71.7, 71.5, 71.3, 62.8, 62.7, 33.2, 31.6, 31.0, 30.9 30.6, 27.5, 23.9, 14.6; HRMS (EI): calculated for C$_{50}$H$_{94}$O$_{26}$[M+Na]$^+$ 1110.6033, found 1110.6037. The $^1$H NMR spectrum of MNA-3 is shown in FIG. 7, and the $^{13}$C NMR spectra of MNA-3 is shown in FIG. 8.

<Preparative Example 4> Synthesis of MNA-4

<4-1> Synthesis of 3,4-O-di-undecyl-1,2:5,6-di-O-isopropylidene-D-mannitol (Compound 4)

3,4-O-di-undecyl-1,2:5,6-di-O-isopropylidene-D-mannitol (compound 4) was synthesized with a yield of 90% according to the method of Example 1-1 using (1R,2R)-1,2-bis((S)-2,2-dimethyl-1,3-dioxolan-4-yl)ethane-1,2-diol as a starting material and undecyl bromide as an alkyl bromide. The $^1$H NMR spectra of the separated product were identical to the data reported in the article by S. Roy et al. (*Colloids surf. A* 2011, 377, 349-355.).

<4-2> Synthesis of 3,4-O-di-undecyl-D-mannitol (Compound 14)

3,4-O-di-undecyl-D-mannitol (compound 14) was synthesized from the compound 4 with a yield of 93% according to the method of Example 1-2. The $^1$H NMR spectra of the separated product were identical to the data reported in the article by J. Walton et al. (*Tetrahedron Lett.* 2006, 47, 737-741.).

<4-3> Synthesis of MNA-4a

A glycosylation reaction was performed according to the method of Example 1-3 to synthesize MNA-4a from the compound 14 with a yield of 70%. $^1$H NMR (400 MHz, CDCl$_3$): δ 8.23-8.20 (m, 4H), 8.09-8.01 (m, 4H), 8.00-7.97 (m, 8H), 7.90-7.79 (m, 6H), 7.72-7.65 (m, 16H), 7.61-7.56 (m, 6H), 7.55-7.51 (m, 16H), 7.48-7.35 (m, 32H), 7.33-7.21 (m, 4H), 5.82-5.74 (m, 2H), 5.61-5.51 (m, 4H), 5.49-5.33 (m, 6H), 4.88-4.74 (m, 2H), 4.48-4.46 (m, 2H), 4.45-4.39 (m, 6H), 4.33-4.20 (m, 6H), 4.09-3.95 (m, 2H), 3.58-3.45 (m, 5H), 3.42-3.34 (m, 2H), 3.29-3.19 (m, 4H), 1.83-1.74 (m, 2H), 1.45-1.12 (m, 32H), 0.86 (t, J=7.6 Hz, 6H); $^{13}$C NMR (100 MHz, CDCl$_3$): δ 166.1, 166.0, 165.7, 165.3, 165.1, 164.9, 133.8, 133.6, 133.5, 133.4, 133.2, 129.9, 129.7, 129.6, 129.4, 129.3, 129.2, 129.1, 128.6, 128.5, 101.5, 100.4, 82.5, 80.2, 73.4, 73.0, 72.8, 72.4, 72.0, 71.7, 71.2, 70.0, 69.9, 63.3, 63.0, 32.1, 30.3, 30.0, 29.8, 29.6, 26.3, 22.9, 14.3.

<4-4> Synthesis of MNA-4

A de-O-benzoylation reaction was performed according to the method of Example 1-4 to synthesize MNA-4, from which a protecting group was removed, from the compound MNA-4a with a yield of 92%. $^1$H NMR (400 MHz, CD$_3$OD): δ 4.51-4.50 (m, 2H), 4.31-4.28 (m, 2H), 4.12-4.09 (m, 2H), 3.98-3.96 (m, 4H), 3.82-3.74 (m, 4H), 3.71-3.64 (m, 3H), 3.64-3.55 (m, 10H), 3.28-3.20 (m, 15H), 3.19-3.06 (m, 5H), 1.49-1.41 (m, 4H), 1.19 (m, 32H), 0.90 (t, J=8.0 Hz, 6H); $^{13}$C NMR (100 MHz, CD$_3$OD): δ 105.2, 104.8, 82.6, 81.0, 78.3, 78.1, 77.9, 75.7, 75.4, 74.5, 71.7, 71.5, 71.3, 62.8, 62.7, 33.2, 31.6, 31.0, 30.9 30.6, 27.4, 23.9, 14.6; HRMS (EI): calculated for C$_{52}$H$_{98}$O$_{26}$[M+Na]$^+$ 1138.6346, found 1138.6341. The $^1$H NMR spectrum of MNA-4 is shown in FIG. 9, and the $^{13}$C NMR spectrum of MNA-4 is shown in FIG. 10.

<Preparative Example 5> Synthesis of MNA-5

<5-1> Synthesis of 3,4-O-di-dodecyl-1,2:5,6-di-O-isopropylidene-D-mannitol (Compound 5)

3,4-O-di-dodecyl-1,2:5,6-di-O-isopropylidene-D-mannitol (compound 5) was synthesized with a yield of 90% according to the method of Example 1-1 using (1R,2R)-1,2-bis((S)-2,2-dimethyl-1,3-dioxolan-4-yl)ethane-1,2-diol as a starting material and dodecyl bromide as an alkyl bromide. The $^1$H NMR spectra of the separated product were identical to the data reported in the article by J. Walton et al. (*Tetrahedron Lett.* 2006, 47, 737-741.).

<5-2> Synthesis of 3,4-O-di-dodecyl-D-mannitol (Compound 15)

3,4-O-di-dodecyl-D-mannitol (compound 15) was synthesized from the compound 5 with a yield of 92% according to the method of Example 1-2. The $^1$H NMR spectra of the separated product were identical to the data reported in the article by J. Walton et al. (*Tetrahedron Lett.* 2006, 47, 737-741.).

<5-3> Synthesis of MNA-5a

A glycosylation reaction was performed according to the method of Example 1-3 to synthesize MNA-5a from the compound 15 with a yield of 65%. $^1$H NMR (400 MHz, CDCl$_3$): δ 8.24-8.21 (m, 4H), 8.12-7.98 (m, 4H), 7.97-7.92 (m, 8H), 7.91-7.89 (m, 6H), 7.87-7.79 (m, 16H), 7.61-7.56 (m, 6H), 7.55-7.43 (m, 16H), 7.41-7.35 (m, 32H), 7.34-7.27 (m, 4H), 5.78-5.74 (m, 2H), 5.57-5.42 (m, 4H), 5.41-5.30 (m, 6H), 4.88-4.74 (m, 2H), 4.48-4.46 (m, 2H), 4.45-4.39 (m, 6H), 4.33-4.20 (m, 6H), 4.01-3.91 (m, 2H), 3.54-3.41 (m, 5H), 3.40-3.32 (m, 2H), 3.31-3.14 (m, 4H), 1.78-1.65 (m, 2H), 1.30-1.10 (m, 36H), 0.86 (t, J=7.6 Hz, 6H); $^{13}$C NMR (100 MHz, CDCl$_3$): δ 166.0, 165.9, 165.7, 165.2, 165.1, 164.9, 133.7, 133.5, 133.4, 133.3, 133.1, 130.1, 130.0, 129.9, 129.8, 129.6, 129.5, 129.3, 129.2, 129.0, 128.9, 128.5, 128.4, 101.4, 100.4, 82.4, 80.2, 73.4, 72.9, 72.8, 72.7, 72.4, 71.9, 71.6, 71.1, 69.9, 69.8, 63.2, 63.0, 32.0, 30.3, 29.9, 29.8, 29.7, 29.5, 26.2, 22.8, 14.2.

<5-4> Synthesis of MNA-5

A de-O-benzoylation reaction was performed according to the method of Example 1-4 to synthesize MNA-5, from which a protecting group was removed, from the compound MNA-5a with a yield of 92%. $^1$H NMR (400 MHz, CD$_3$OD): δ 4.57-4.55 (m, 2H), 4.35-4.33 (m, 2H), 4.15-4.02 (m, 2H), 4.00-3.97 (m, 4H), 3.86-3.77 (m, 4H), 3.76-3.69 (m, 3H), 3.67-3.59 (m, 10H), 3.33-3.22 (m, 15H), 3.21-3.13 (m, 5H), 1.51-1.46 (m, 4H), 1.23 (m, 36H), 0.90(t, J =8.0 Hz, 6H); $^{13}$C NMR (100 MHz, CD$_3$OD): δ 105.2, 104.8, 82.7, 81.0, 78.2, 78.1, 77.8, 75.6, 75.3, 74.5, 71.7, 71.5, 71.3, 62.8, 62.6, 33.2, 31.6, 30.9 30.6, 27.4, 23.8, 14.6; HRMS (EI): calculated for C$_{54}$H$_{102}$O$_{26}$[M+Na]$^+$ 1166.6659, found 1166.6658. The $^1$H NMR spectrum of MNA-5 is shown in FIG. 11, and the $^{13}$C NMR spectrum of MNA-5 is shown in FIG. 12.

<Preparative Example 6> Synthesis of MNA-6

<6-1> Synthesis of 3,4-O-di-tridecyl-1,2:5,6-di-O-isopropylidene-D-mannitol (compound 6)

3,4-O-di-tridecyl-1,2:5,6-di-O-isopropylidene-D-mannitol (compound 6) was synthesized with a yield of 92% according to the method of Example 1-1 using (1R,2R)-1,2-bis((S)-2,2-dimethyl-1,3-dioxolan-4-yl)ethane-1,2-diol as a starting material and tridecyl bromide as an alkyl bromide. $^1$H NMR (400 MHz, CDCl$_3$): δ4.25-4.20 (m, 2H), 4.19-4.05 (m, 2H), 3.97-3.91 (m, 2H), 3.61-3.51 (m, 4H), 3.34-3.31

(m, 2H), 1.57-1.53 (m, 4H), 1.41 (s, 6H), 1.34 (s, 6H), 1.25 (m, 40H), 0.88 (t, J=8.0 Hz, 6H); $^{13}$C NMR (100 MHz, CDCl$_3$): δ 108.6, 80.6, 76.0, 73.6, 67.0, 58.7, 33.0, 32.1, 30.5, 29.9, 29.8, 29.7, 26.9, 26.3, 26.0, 25.6, 22.9, 14.3.

<6-2>Synthesis of 3,4-O-di-tridecyl-D-mannitol (Compound 16)

3,4-O-di-tridecyl-D-mannitol (compound 16) was synthesized from the compound 6 with a yield of 92% according to the method of Example 1-2. $^1$H NMR (400 MHz, CDCl$_3$): δ 4.03-3.97 (m, 2H), 3.90-3.82 (m, 2H), 3.81-3.75 (m, 2H), 3.73-3.62 (m, 4H), 3.60-3.33 (m, 2H), 1.57-1.54 (m, 4H), 1.25 (m, 40H), 0.88 (t, J=8.0 Hz, 6H); $^{13}$C NMR (100 MHz, CDCl$_3$): δ 108.6, 80.4, 79.2, 76.1, 72.4, 71.7, 66.2, 63.4, 30.2, 29.8, 29.7, 29.6, 26.7, 26.3, 25.3, 22.9, 14.3.

<6-3>Synthesis of MNA-6a

A glycosylation reaction was performed according to the method of Example 1-3 to synthesize MNA-6a from the compound 16 with a yield of 60%. $^1$11 NMR (400 MHz, CDCl$_3$): δ 8.23-8.21 (m, 4H), 8.20-7.98 (m, 4H), 7.97-7.92 (m, 8H), 7.91-7.89 (m, 6H), 7.87-7.79 (m, 16H), 7.61-7.56 (m, 6H), 7.55-7.43 (m, 16H), 7.40-7.35 (m, 32H), 7.34-7.27 (m, 4H), 5.77-5.74 (m, 2H), 5.57-5.42 (m, 4H), 5.41-5.30 (m, 6H), 4.88-4.74 (m, 2H), 4.48-4.46 (m, 2H), 4.45-4.39 (m, 6H), 4.33-4.20 (m, 6H), 4.01-3.91 (m, 2H), 3.54-3.41 (m, 5H), 3.40-3.32 (m, 2H), 3.31-3.14 (m, 4H), 1.81-1.34 (m, 2H), 1.24-1.12 (m, 40H), 0.86 (t, J=7.6 Hz, 6H); $^{13}$C NMR (100 MHz, CDCl$_3$): δ 166.0, 165.9, 165.7, 165.2, 165.1, 164.9, 133.7, 133.6, 133.4, 133.3, 133.1, 130.2, 130.1, 130.0, 129.9, 129.8, 129.6, 129.5, 129.3, 129.2, 129.0, 128.9, 128.5, 128.4, 128.1, 101.4, 100.4, 98.4, 82.4, 80.1, 73.4, 72.9, 72.7, 72.4, 71.9, 71.6, 71.4, 71.1, 69.9, 69.8, 69.5, 63.2, 63.0, 62.6, 60.5, 32.0, 30.3, 29.9, 29.8, 29.7, 29.5, 26.2, 22.8, 14.2.

<6-4>Synthesis of MNA-6

A de-O-benzoylation reaction was performed according to the method of Example 1-4 to synthesize MNA-6, from which a protecting group was removed, from the compound MNA-6a with a yield of 90%. $^1$H NMR (400 MHz, CD$_3$OD): δ 4.55-4.53 (m, 2H), 4.31-4.30 (m, 2H), 4.13-4.11 (m, 2H), 4.00-3.97 (m, 4H), 3.79-3.72 (m, 4H), 3.70-3.64 (m, 3H), 3.63-3.56 (m, 10H), 3.30-3.21 (m, 15H), 3.20-3.10 (m, 5H), 1.46-1.44 (m, 4H), 1.20 (m, 40H), 0.90 (t, J =8.0 Hz, 6H); $^{13}$C NMR (100 MHz, CD$_3$OD): δ 105.2, 104.8, 82.7, 81.0, 78.3, 78.1, 77.9, 75.7, 75.4, 74.5, 71.7, 71.5, 71.3, 62.8, 62.7, 33.2, 31.6, 31.0, 30.9 30.6, 27.5, 23.8, 14.6; HRMS (EI): calculated for C$_{56}$H$_{106}$O$_{26}$[M+Na]$^+$ 1194.6972, found 1194.6968. The $^1$H NMR spectrum of MNA-6 is shown in FIG. 13, and the $^{13}$C NMR spectum of MNA-6 is shown in FIG. 14.

<Preparative Example 7>Synthesis of MNA-7

<7-1>Synthesis of 3,4-O-di-tetradecyl-1,2:5,6-di-O-isopropylidene-D-mannitol (Compound 7)

3,4-O-di-tetradecyl-1,2:5,6-di-O-isopropylidene-D-mannitol (compound 7) was synthesized with a yield of 92% according to the method of Example 1-1 using (1R,2R)-1,2-bis((S)-2,2-dimethyl-1,3-dioxolan-4-yl)ethane-1,2-diol as a starting material and tetradecyl bromide as an alkyl bromide. The $^1$H NMR spectra of the separated product were identical to the data reported in the article by S. Roy et al. (*Colloids surf A* 2011, 377, 349-355.).

<7-2>Synthesis of 3,4-O-di-tetradecyl-D-mannitol (Compound 17)

3,4-O-di-tetradecyl-D-mannitol (compound 17) was synthesized from the compound 7 with a yield of 92% according to the method of Example 1-2. The $^1$H NMR spectra of the separated product were identical to the data reported in the article by S. Roy et al. (*Colloids surf A* 2011, 377, 349-355.).

<7-3>Synthesis of MNA-7a

A glycosylation reaction was performed according to the method of Example 1-3 to synthesize MNA-7a from the compound 17 with a yield of 54%. $^1$H NMR (400 MHz, CDCl$_3$): δ 8.24-8.23 (m, 4H), 8.12-7.98 (m, 4H), 7.97-7.93 (m, 8H), 7.91-7.89 (m, 6H), 7.88-7.83 (m, 16H), 7.61-7.56 (m, 6H), 7.55-7.43 (m, 16H), 7.41-7.35 (m, 32H), 7.34-7.27 (m, 4H), 5.79-5.77 (m, 2H), 5.57-5.54 (m, 4H), 5.49-5.43 (m, 6H), 5.30-5.21 (m, 2H), 4.90-4.79 (m, 2H), 4.60-4.39 (m, 6H), 4.33-4.20 (m, 6H), 4.01-3.91 (m, 2H), 3.56-3.49 (m, 5H), 3.40-3.32 (m, 2H), 3.31-3.15 (m, 4H), 1.51-1.32 (m, 2H), 1.27-1.12 (m, 44H), 0.86 (t, J=7.6 Hz, 6H); $^{13}$C NMR (100 MHz, CDCl$_3$): δ 166.2, 166.1, 166.0, 165.9, 165.7, 165.2, 165.1, 164.9, 133.7, 133.6, 133.5, 133.4, 133.3, 133.1, 130.2, 130.1, 130.0, 129.9, 129.8, 129.7, 129.6, 129.3, 129.2, 129.1, 129.0, 128.9, 128.8, 128.5, 128.4, 128.3, 128.1, 101.5, 100.4, 82.4, 80.2, 73.4, 73.0, 72.9, 72.8, 72.4, 71.9, 71.7, 71.1, 70.0, 69.9, 63.2, 63.0, 32.0, 30.3, 29.9, 29.8, 29.5, 26.2, 22.8, 14.2.

<7-4>Synthesis of MNA-7

A de-O-benzoylation reaction was performed according to the method of Example 1-4 to synthesize MNA-7, from which a protecting group was removed, from the compound MNA-7 with a yield of 92%. a $^1$H NMR (400 MHz, CD$_3$OD): δ 4.29-4.27 (m, 2H), 4.11-4.09 (m, 2H), 3.98-3.96 (m, 2H), 3.80-3.77 (m, 4H), 3.67-3.63 (m, 4H), 3.62-3.59 (m, 3H), 3.58-3.53 (m, 10H), 3.27-3.17 (m, 15H), 3.16-3.08 (m, 5H), 1.55-1.46 (m, 4H), 1.21 (m, 44H), 0.90 (t, J=8.0 Hz, 6H); $^{13}$C NMR (100 MHz, CD$_3$OD): δ 105.2, 104.8, 82.7, 81.0, 78.3, 78.1, 77.9, 75.7, 75.4, 74.5, 71.7, 71.6, 71.3, 62.8, 62.7, 33.2, 31.6, 30.9 30.6, 27.5, 23.9, 14.6; HRMS (EI): calculated for C$_{58}$H$_{110}$O$_{26}$[M+Na]$^+$ 1222.7285, found 1222.7283. The $^1$H NMR spectrum of MNA-7 is shown in FIG. 15, and the $^{13}$C NMR spectrum of MNA-7 is shown in FIG. 16.

<Preparative Example 8>Synthesis of MNA-8

<8-1,2>Synthesis of 3,4-O-di-tetradecyl-D-mannitol (compound 8)

3,4-O-di-pentadecyl-1,2:5,6-di-O-isopropylidene-D-mannitol (compound 8) was synthesized according to the method of Example 1-1 using (1R,2R)-1,2-bis((S)-2,2-dimethyl-1,3-dioxolan-4-yl)ethane-1,2-diol as a starting material and pentadecyl bromide as an alkyl bromide, and the next steps were then carried out without purification. 3,4-O-di-tetradecyl-D-mannitol (compound 18) was synthesized from the compound 8 with a in a yield of 76% according to the method of Example 1-2 (two steps). The $^1$H NMR spectra of the separated product were identical to the data reported in the article by S. Roy et al. (*Colloids surf A* 2011, 377, 349-355.).

<8-3>Synthesis of MNA-8a

A glycosylation reaction was performed according to the method of Example 1-3 to synthesize MNA-8a from the compound 18 with a yield of 54%. $^1$H NMR (400 MHz, CDCl$_3$): δ 8.23-8.21 (m, 4H), 8.20-7.99(m, 4H), 7.98-7.93 (m, 8H), 7.92-7.88 (m, 6H), 7.87-7.78 (m, 16H), 7.56-7.38 (m, 6H), 7.37-7.34 (m, 16H), 7.33-7.29 (m, 32H), 7.27-7.25(m, 4H), 5.77-5.74 (m, 2H), 5.57-5.51 (m, 4H), 5.47-5.39 (m, 6H), 4.80-4.76 (m, 2H), 4.48-4.46 (m, 2H), 4.32-4.29 (m, 6H), 4.28-4.22 (m, 6H), 4.01-3.94 (m, 2H), 3.54-3.41 (m, 5H), 3.40-3.32 (m, 2H), 3.31-3.14 (m, 4H), 1.81-1.34 (m, 2H), 1.24-1.12 (s, 48H), 0.87 (t, J=7.6 Hz, 6H); $^{13}$C NMR (100 MHz, CDCl$_3$): δ 165.9, 165.8, 165.6, 165.1, 165.0, 164.8, 133.6, 133.4, 133.2, 133.1, 130.2, 130.0, 129.8, 129.7, 129.5, 129.2, 129.0, 128.9, 128.7, 128.5, 128.4, 101.4, 100.3, 91.4, 82.4, 80.1, 73.3, 72.9, 72.8, 72.7, 72.3, 71.8, 71.6, 71.1, 69.9, 69.8, 63.2, 62.9, 60.5, 32.0, 30.2, 29.9, 29.8, 29.7, 29.4, 26.2, 22.8, 14.2.

<8-4>Synthesis of MNA-8

A de-O-benzoylation reaction was performed according to the method of Example 1-4 to synthesize MNA-8, from which a protecting group was removed, from the compound MNA-8a with a yield of 90%. $^1$H NMR (400 MHz, CD$_3$OD): δ 4.65-4.62 (m, 2H), 4.42-4.37 (m, 2H), 4.22-4.19 (m, 2H), 4.13-4.04 (m, 2H), 3.91-3.86 (m, 4H), 3.85-3.72 (m, 4H), 3.71-3.68 (m, 3H), 3.67-3.65 (m, 10H), 3.37-3.25 (m, 5H), 3.28-3.19(m, 15H), 1.56-1.48 (m, 4H), 1.28 (s, 48H), 0.89 (t, J=8.0 Hz, 6H); $^{13}$C NMR (100 MHz, CD$_3$OD): δ 105.2, 104.8, 82.7, 81.0, 78.3, 78.1, 77.9, 75.7, 75.4, 74.5, 71.7, 71.5, 71.3, 62.8, 62.7, 33.2, 31.6, 31.0, 30.9 30.6, 27.5, 23.8, 14.6.

<Preparative Example 9>Synthesis of MNA-9

<9-1,2>Synthesis of 3,4-O-di-hexadecyl-D-mannitol (compound 19)

3,4-O-di-hexadecyl-1,2:5,6-di-O-isopropylidene-D-mannitol (compound 9) was synthesized according to the method of Example 1-1 using (1R,2R)-1,2-bis((S)-2,2-dimethyl-1,3-dioxolan-4-yl)ethane-1,2-diol as a starting material and hexadecyl bromide as an alkyl bromide, and the next steps were then carried out without purification. 3,4-O-di-hexadecyl-D-mannitol (compound 19) was synthesized from the compound 9 with a yield of 76% according to the method of Example 1-2 (two steps). The $^1$H NMR spectra of the separated product were identical to the data reported in the article by S. Roy et al. (*Colloids surf A* 2011, 377, 349-355.).

<9-3>Synthesis of MNA-9a

A glycosylation reaction was performed according to the method of Example 1-3 to synthesize MNA-9a from the compound 19 with a yield of 52%. $^1$H NMR (400 MHz, CDCl$_3$): δ 8.23-8.21 (m, 4H), 8.20-7.99(m, 4H), 7.98-7.93 (m, 8H), 7.92-7.88 (m, 6H), 7.87-7.78 (m, 16H), 7.56-7.38 (m, 6H), 7.37-7.34 (m, 16H), 7.33-7.29 (m, 32H), 7.27-7.25 (m, 4H), 5.77-5.74 (m, 2H), 5.57-5.51 (m, 4H), 5.47-5.39 (m, 6H), 4.80-4.76 (m, 2H), 4.48-4.46 (m, 2H), 4.32-4.29 (m, 6H), 4.28-4.22 (m, 6H), 4.01-3.94 (m, 2H), 3.54-3.41 (m, 5H), 3.40-3.32 (m, 21-1), 3.31-3.14 (m, 4H), 1.81-1.34 (m, 2H), 1.24-1.12 (s, 48H), 0.87 (t, J=7.6 Hz, 6H); $^{13}$C NMR (100 MHz, CDCl$_3$): δ 165.9, 165.8, 165.6, 165.1, 165.0, 164.8, 133.6, 133.4, 133.2, 133.1, 130.2, 130.0, 129.8, 129.7, 129.5, 129.2, 129.0, 128.9, 128.7, 128.5, 128.4, 101.4, 100.3, 91.4, 82.4, 80.1, 73.3, 72.9, 72.8, 72.7, 72.3, 71.8, 71.6, 71.1, 69.9, 69.8, 63.2, 62.9, 60.5, 32.0, 30.2, 29.9, 29.8, 29.7, 29.4, 26.2, 22.8, 14.2.

<9-4>Synthesis of MNA-9

A de-O-benzoylation reaction was performed according to the method of Example 1-4 to synthesize MNA-9, from which a protecting group was removed from the compound MNA-9a with a yield of 92%. $^1$H NMR (400 MHz, CD$_3$OD): 6 4.65-4.62 (m, 2H), 4.42-4.37 (m, 2H), 4.22-4.19 (m, 2H), 4.13-4.04 (m, 2H), 3.91-3.86 (m, 4H), 3.85-3.72 (m, 4H), 3.71-3.68 (m, 3H), 3.67-3.65 (m, 10H), 3.37-3.25 (m, 5H), 3.28-3.19(m, 15H), 1.56-1.48 (m, 4H), 1.28 (s, 48H), 0.89 (t, J=8.0 Hz, 6H); $^{13}$C NMR (100 MHz, CD$_3$OD): δ 105.2, 104.8, 82.7, 81.0, 78.3, 78.1, 77.9, 75.7, 75.4, 74.5, 71.7, 71.5, 71.3, 62.8, 62.7, 33.2, 31.6, 31.0, 30.9 30.6, 27.5, 23.8, 14.6.

<Preparative Example 10>Synthesis of MNA-10

<10-1,2>Synthesis of 3,4-O-di-heptadecyl-D-mannitol (Compound 20)

3,4-O-di-heptadecyl-1,2:5,6-di-O-isopropylidene-D-mannitol (compound 10) was synthesized according to the method of Example 1-1 using (1R,2R)-1,2-bis((S)-2,2-dimethyl-1,3-dioxolan-4-yl)ethane-1,2-diol as a starting material and heptadecyl bromide as an alkyl bromide, and the next steps were then carried out without purification. 3,4-O-di-heptadecyl-D-mannitol (compound 20) was synthesized from the compound 10 with a yield of 75% according to the method of Example 1-2 (two steps). The $^1$H NMR spectra of the separated product were identical to the data reported in the article by S. Roy et al. (*Colloids surf. A* 2011, 377, 349-355.).

<10-3>Synthesis of MNA-10a

A glycosylation reaction was performed according to the method of Example 1-3 to synthesize MNA-10a from the compound 20 with a yield of 50%. $^1$H NMR (400 MHz, CDCl$_3$): δ 8.23-8.21 (m, 4H), 8.20-7.99(m, 4H), 7.98-7.93 (m, 8H), 7.92-7.88 (m, 6H), 7.87-7.78 (m, 16H), 7.56-7.38 (m, 6H), 7.37-7.34 (m, 16H), 7.33-7.29 (m, 32H), 7.27-7.25 (m, 4H), 5.77-5.74 (m, 2H), 5.57-5.51 (m, 4H), 5.47-5.39 (m, 6H), 4.80-4.76 (m, 2H), 4.48-4.46 (m, 2H), 4.32-4.29 (m, 6H), 4.28-4.22 (m, 6H), 4.01-3.94 (m, 2H), 3.54-3.41 (m, 5H), 3.40-3.32 (m, 2H), 3.31-3.14 (m, 4H), 1.81-1.34 (m, 2H), 1.24-1.12 (s, 48H), 0.87 (t, J =7.6 Hz, 6H); $^{13}$C NMR (100 MHz, CDCl$_3$): δ 165.9, 165.8, 165.6, 165.1, 165.0, 164.8, 133.6, 133.4, 133.2, 133.1, 130.2, 130.0, 129.8, 129.7, 129.5, 129.2, 129.0, 128.9, 128.7, 128.5, 128.4, 101.4, 100.3, 91.4, 82.4, 80.1, 73.3, 72.9, 72.8, 72.7, 72.3, 71.8, 71.6, 71.1, 69.9, 69.8, 63.2, 62.9, 60.5, 32.0, 30.2, 29.9, 29.8, 29.7, 29.4, 26.2, 22.8, 14.2.

<10-4>Synthesis of MNA-10

A de-O-benzoylation reaction was performed according to the method of Example 1-4 to synthesize MNA-10, from which a protecting group was removed, from the compound MNA-10a with a yield of 92%. $^1$H NMR (400 MHz, CD$_3$OD): δ 4.65-4.62 (m, 2H), 4.42-4.37 (m, 2H), 4.22-4.19 (m, 2H), 4.13-4.04 (m, 2H), 3.91-3.86 (m, 4H), 3.85-3.72 (m, 4H), 3.71-3.68 (m, 3H), 3.67-3.65 (m, 10H), 3.37-3.25 (m, 5H), 3.28-3.19(m, 15H), 1.56-1.48 (m, 4H), 1.28 (s, 48H), 0.89 (t, J=8.0 Hz, 6H); $^{13}$C NMR (100 MHz, CD$_3$OD): δ 105.2, 104.8, 82.7, 81.0, 78.3, 78.1, 77.9, 75.7, 75.4, 74.5, 71.7, 71.5, 71.3, 62.8, 62.7, 33.2, 31.6, 31.0, 30.9 30.6, 27.5, 23.8, 14.6.

Example 2

Characteristics of MNAs

To determine characteristics of the MNAs of Preparative Example 1 to 10 synthesized according to the synthesis method of Example 1, the molecular weights (M.W.) and critical micellar concentrations (CMCs) of the MNAs and the hydrodynamic radii (R$_h$) of the formed micelles were measured.

Specifically, the critical micellar concentration (CMC) was measured using a hydrophobic fluorescence stain (diphenylhexatriene (DPH)), and the hydrodynamic radii (R$_h$) of the micelles formed by each of the preparations were measured by a dynamic light scattering (DLS) experiment. The measured results were compared to those of DDM that is a conventional amphipathic molecule (a detergent), and are listed in Table 1.

TABLE 1

| Detergent | M.W. | CMC (mM) | CMC (% by weight) | R$_h$ (nm) |
|---|---|---|---|---|
| MNA-1 | 1055.2 | Approximately 0.15 | Approximately 0.016 | 2.3 ± 0.13 |
| MNA-2 | 1083.2 | Approximately 0.05 | Approximately 0.0054 | 2.5 ± 0.05 |
| MNA-3 | 1111.3 | Approximately 0.015 | Approximately 0.0017 | 2.7 ± 0.04 |
| MNA-4 | 1139.3 | Approximately 0.006 | Approximately 0.0007 | 2.9 ± 0.12 |
| MNA-5 | 1167.4 | Approximately 0.004 | Approximately 0.0005 | 3.0 ± 0.01 |
| MNA-6 | 1195.4 | Approximately 0.002 | Approximately 0.0002 | 3.3 ± 0.04 |
| MNA-7 | 1233.5 | Approximately 0.001 | Approximately 0.0001 | 3.3 ± 0.08 |
| MNA-8 | 1251.53 | Approximately 0.003 | Approximately 0.0003 | 3.5 ± 0.1 |
| MNA-9 | 1279.58 | Approximately 0.001 | Approximately 0.0001 | 3.8 ± 0.1 |
| MNA-10 | 1307.64 | Approximately 0.001 | Approximately 0.0001 | 4.1 ± 0.2 |
| DDM | 510.1 | Approximately 0.17 | Approximately 0.0087 | 3.4 ± 0.03 |

The measurement results of the critical micellar concentrations (CMCs) of the MNAs showed that MNA-1 had a CMC value of 150 μM (0.016% by weight), MNA-2 had a CMC value of 50 μM (0.0054% by weight), MNA-3 had a CMC value of 15 μM (0.0017% by weight), MNA-4 had a CMC value of 6 μM (0.0007% by weight), MNA-5 had a CMC value of 4 μM (0.0005% by weight), MNA-6 had a CMC value of 2 μM (0.0002% by weight), MNA-7 had a CMC value of 1 μM (0.0001% by weight), MNA-8 had a CMC value of 3 μM (0.0003% by weight), MNA-9 had a CMC value of 1 μM (0.0001% by weight), and MNA-10 had a CMC value of 1 μM (0.0001% by weight). That is, it was revealed that the CMC value of MNA-1 was 150 μM which was substantially similar to that of DDM, but the CMC values of MNA-2 to MNA-10 were in a range of 1 to 50 μM which was smaller than that of DDM having a CMC value of 170 μM. Also, the CMC values tended to decrease with an increase in lengths of the alkyl chains of the compounds. Here, it was confirmed that MNA-1 having the shortest alkyl chain (C8) had a CMC value of approximately 50 μM (approximately 0.016% by weight), and MNA-7, MNA-9 and MNA-10 having long alkyl chains (C14, C16, and C17) had a CMC value of 1 μM (approximately 0.0001% by weight). Therefore, it could be seen that, since the micelles were easily formed even when the MNAs were used in small quantities, the MNAs may be used in an amount smaller than that of DDM to study the membrane proteins and are more soluble in water than DDM.

The measurement results of the hydrodynamic radii (R$_h$) of the micelles formed by the MNAs showed that MNA-1 had a measured R$_h$ of 2.3 nm, MNA-2 had a measured R$_h$ of 2.5 nm, MNA-3 had a measured R$_h$ of 2.7 nm, MNA-4 had a measured R$_h$ of 2.9 nm, MNA-5 had a measured R$_h$ of 3.0 nm, MNA-6 had a measured R$_h$ of 3.3 nm, MNA-7 had a measured R$_h$ of 3.3 nm, MNA-8 had a measured R$_h$ of 3.5 nm, MNA-9 had a measured R$_h$ of 3.8 nm, and MNA-10 had a measured R$_h$ of 4.1 nm. Generally, the sizes of the micelles formed by the MNAs were similar to or smaller than that of DDM and tended to increase according to the lengths of the alkyl chains. MNA-1 had the smallest micelle size (2.3 nm), and MNA-10 had the highest micelle size (4.1 nm).

Meanwhile, the size distributions of the micelles formed by the MNAs were measured using DLS, and the measurement results are shown in FIG. 17. The MNAs were used at a content of 1.0% by weight. As a result, it was revealed that the micelles of the MNAs had one cluster similar to DDM.

From these results, it could be seen that the micelles were easily formed even when the MNAs of the present invention were used in a small quantity since the MNAs had lower CMC values than DDM and thus had a much higher tendency toward self-assembly than DDM and that the membrane proteins were more easily separated from the micelles of the amphipathic molecules according to the present invention since the sizes of the micelles formed by the MNAs were smaller than those of DDM.

Example 3

Evaluation of abilities of MNAs to Stabilize Structure of Membrane Protein (Bor1)

An experiment for measuring the structural stability of a boron transporter (Bor1) by the MNAs was performed. The structural stability of Bor1 was measured using heat fluorescence size exclusion chromatography (hFSEC), and the concentrations of the MNAs and DDM were CMC plus 0.04% by weight.

Specifically, Bor1 of *Arabidopsis thaliana* was expressed in *Saccharomyces cerevisiae* FGY217 cells as a fusion protein having a C-terminal GFP-His tag. The cells were grown in a -URA medium supplemented with 0.1% glucose. Expression of proteins was induced by adding 2% galactose, and the cells were then cultured at 20° C. for 18 hours. Here, the cell culture was carried out according to the method described in the article by D. Drew et al. (*Nat. Protoc.* 2008, 3, 784-798.). The cells were collected to prepare membranes, and the cell collection was carried out according to the method described in the article by J. Leung et al. (*Protein Expr. Purif.* 2010, 72, 139-146.). The membranes including the Bor1-GFP fusion protein were diluted with phosphate-buffered saline (PBS, pH 7.4) until the final concentration of the total proteins reached 2.8 mg/mL. In this case, 1% by weight of DDM or 1% by weight of MNA (MNA-1, MNA-2, MNA-3, MNA-4, MNA-5, MNA-6, or MNA-7) was added to the PBS. Samples were incubated for an hour while shaking at 4° C., and insoluble materials were then removed by centrifugation at 14,000 g and 4° C. for an hour. The supernatant including the dissolved protein samples was heated at 40° C. for 10 minutes, and the strongly aggregated proteins were removed by centrifugation at 14,000 g and 4° C. for 10 minutes. 200 µL of the supernatant of the samples was injected into a Superose 6 10/300 column equilibrated with 20 mM Tris (pH 7.5), 150 mM NaCl, and 0.03% DDM. Each of elution fractions was collected in 200 µL fractions at a retention volume of 6.4 mL (e.g., 6.4 mL after elusion) in a clear bottom 96-well plate. The GFP fluorescence of each of the fractions was measured at an excitation wavelength of 470 nm and an emission wavelength of 512 nm.

The measurement results are shown in FIG. 18, the peaks observed at the retention volume (40 mL) corresponded to the Bor1 protein following heat treatment. Under the same conditions, DDM had a weak peak observed at 40 mL and had a peak (8 mL) showing a significant level of protein aggregation. Therefore, the Bor1 extracted with DDM was considered to have a significant level of protein aggregation. MNA-4 had a tendency to have a level of protein aggregation similar to DDM, and MNA-5 and MNA-6 had a lower level of Bor1 aggregation than DDM and exhibited superior characteristics due to the very strong peaks corresponding to Bor1. Also, MNA-7 had excellent effects by having a lower level of Bor1 aggregation than DDM, but among the MNAs, MNA-6 had the best effect on stabilization of the Bor1, considering the level of protein aggregation and the size of the peaks corresponding to the target protein. Such high peaks of the membrane protein may be observed only when the protein extraction efficiency is also high. Therefore, it could be seen that the MNAs (MNA-5, MNA-6, and MNA-7) also had excellent membrane protein extraction efficiency. In fact, MNA-5 had an extraction efficiency of 60%, and MNA-6 and MNA-7 had an extraction efficiency of 70 to 80% which were similar to that of DDM having an extraction efficiency of 80%.

From these results, it could be seen that the MNAs had a superior ability to stabilize a structure of Bor1 compared to the conventional DDM and thus was able to be used to extract or stabilize the membrane proteins.

Example 4

Evaluation of Abilities of MNAs to Stabilize Structure of Membrane Protein (LeuT)

An experiment for measuring the structural stability of a leucine transporter (LeuT) by the MNAs was performed. The activities of the LeuT protein was measured by a scintillation proximity assay (SPA) using a substrate ([$^3$H]-Leu), and the concentrations of the MNAs and DDM used were (a) CMC plus 0.04% by weight, or (b) CMC plus 0.02% by weight.

Specifically, a wild-type leucine transporter (LeuT) was purified from *Aquifex aeolicus* according to the method disclosed in the article by G. Deckert et al. (*Nature* 1998, 392, 353-358.). The LeuT was expressed in *E. coli* C41 (DE3) transformed with pET16b coding for a C-terminal 8×His-tagged transporter (an expression plasmid was kindly provided by Dr E. Gouaux, Vollum Institute, Portland, Oreg., USA). In summary, a protein was isolated, and solubilized in 1.0% by weight of DDM. Then, the protein was bound to an Ni$^{2+}$-NTA resin (Life Technologies, Denmark) and eluted with 20 mM Tris-HCl (pH 8.0), 1 mM NaCl, 199 mM KCl, 0.05% DDM, and 300 mM imidazole. Subsequently, approximately 0.8 mg/ml of a protein stock was diluted with an equivalent buffer having no DDM and imidazole but supplemented with MNAs (MNA-5, MNA-6 or MNA-6) or DDM (control) so that the final concentration reached CMC plus 0.04% by weight or CMC plus 0.2% by weight. Protein samples were stored at room temperature, and centrifuged for a given period of time, and the activities of the proteins were determined by measuring [$^3$H]-Leu binding using a scintillation proximity assay (SPA) (M. Quick et al., *Proc. Natl, Acad. Sci. U.S.A.* 2007, 104, 3603-3608.). SPA was performed using 5 µL of each of the protein samples, 20 nM [$^3$H]-Leu, and 1.25 mg/ml copper chelate (both commercially available from PerkinElmer, Denmark) dissolved in a buffer including 450 mM NaCl and the concentration of each of the test compounds. The [$^3$H]-Leu binding was measured using a MicroBeta liquid scintillation counter (PerkinElmer).

As shown in FIG. 19, the measurement results of substrate-binding abilities of LeuT dissolved in each of the MNAs over incubation time showed that MNA-6 had the best substrate-binding abilities when present at a content of CMC plus 0.04% by weight, and MNA-5 had the best ligand-binding abilities when present at a content of CMC plus 0.2% by weight. At each concentration, MNA-7 had an ability to stabilize LeuT at a level similar to DDM.

From these results, it could be seen that MNA-5 and MNA-6 of the present invention had a superior ability to stabilize LeuT compared to the DDM, and MNA-7 had an ability to stabilize LeuT at a level similar to DDM.

Example 5

Evaluation of Abilities of Compounds According to the Present Invention to Stabilize Structure of Membrane Protein (($\beta_2$AR)

Experiments for measuring the structural stabilities of a human β2 adrenergic receptor ($\beta_2$AR), a G-protein-coupled receptor (GPCR), in the MNAs were performed.

<5-1>Measurement of mBBr-$\beta_2$AR Dissolved in MNAs and DDM Micelles According to the Presence of Full Agonist (ISO) or a Combination of ISO and G-Protein Experiments for measuring the structural changes and structural stabilities of mBBr-$\beta_2$AR by the MNAs (MNA-5, MNA-6, MNA-7) and DDM according to the presence or absence of a full agonist (isopreoterenol (ISO)) or a combination of ISO and G-protein were performed.

Specifically, $\beta_2$AR dissolved in 0.1% DDM was purified according to the method disclosed in the article by D. M. Rosenbaum et al. (*Science* 2007, 318, 1266-1273) and then concentrated to a concentration of approximately 1 mg/mL. 0.5 µL of non-ligand BI (agonist)-coupled monobromobimane (mBBr)-labeled $\beta_2$AR dissolved in 50 µM of 0.1% DDM was diluted with a buffer of the MNAs (MNA-5, MNA-6 or MNA-7) which were present at a content of 500 µL CMC plus 0.04% by weight or a content of CMC plus 0.2% by (finally to a 50 nM concentration of the receptor) at room temperature for 10 minutes. The mBBr-labeled $\beta_2$AR was cultured for 30 minutes, and the mBBr spectra thereof were measured and compared to the spectra of the mBBr-labeled receptor dissolved in 0.1% DDM. The fluorescence of the mBBr-labeled $\beta_2$AR was measured at 370 nm and thus determined by emission from 430 to 510 nm at 1-nm increments with 1 nm s$^{-1}$ integration using a Spex FluoroMax-3 spectrofluorometer (Jobin Yvon Inc.) which was run in a photon counting mode through a 4-nm emission bandwidth pass. mBBr dissolved in DDM was used as the positive control.

Meanwhile, a G protein coupling test was performed using the following method. A change in fluorescence influenced by a local structural change at a proximal portion of transmembrane helix 6 (TM6) was measured using $\beta_2$AR labeled with monobromobimane (mBBr) (mainly at Cys$^{265}$). This followed the method proposed by S. E. Mansoor et al. (*Biochemistry* 2002, 41, 2475-2484.). 0.5 μL of 50 μM non-ligand mBBr-labeled receptor was diluted with 500 μL of a 20×CMC MNA-5, MNA-6 or MNA-7 buffer (finally to a 50 nM concentration of the receptor) at room temperature for 10 minutes. Then, 2 μM isopreoterenol (ISO) was added, and the resulting mixture was cultured again for 10 minutes. 250 nM Gs was additionally added, the resulting mixture was cultured at room temperature for 15 minutes, and the mBB-$\beta_2$AR fluorescence was then measured at 370 nm. Thus, the mBB-$\beta_2$AR fluorescence was determined by emission from 430 to 510 nm at 1-nm increments with 1 nm s$^{-1}$ integration using a Spex FluoroMax-3 spectrofluorometer (Jobin Yvon Inc.) which was run in a photon counting mode set at a 4-nm emission bandwidth pass. mBBr dissolved in DDM was used as the positive control. Data was presented as an average of three separate experiments performed in triplicate.

As shown in FIG. 20, when the full agonist, isopreoterenol (ISO), was present, the bimane spectra of the receptor dissolved in MNA-5, MNA-6, or MNA-7 were similar to those of the receptor dissolved in DDM. Also, when a combination of ISO and G-protein was used, the bimane fluorescence spectra of the mBBr-$\beta_2$AR dissolved in MNA-6 or MNA-7 were similar to those of the $\beta_2$AR dissolved in DDM, but MNA-5 had a slightly higher fluorescence intensity than DDM.

These results showed that the structure and functions of the receptor were maintained effectively when MNA-5, MNA-6, or MNA-7 was used. As such, a decrease in the fluorescence intensity and a change in the maximum emission wavelengths in the presence of ISO and G-protein mean the occurrence of a structural change from an inactive to active state of the receptor by binding of such molecules (ISO and G-protein), indicating that the structure of $\beta_2$AR dissolved in MNA-5, MNA-6, or MNA-7 behaved in a pattern similar to the receptors present in the cell membranes.

<5-2>Measurement of mBBr-$\beta_2$AR at Concentration Below CMC

Experiments for comparing the structural changes of the $\beta_2$AR protein by the MNAs and DDM at a concentration below CMCs of the amphipathic molecules were performed.

Specifically, 0.5 μL of a non-ligand mBBr-labeled receptor dissolved at 50 μNI in a 20×CMC concentration of MNA-5, MNA-6, or MNA-7 was diluted with 500 μL of an NH buffer (20 mM HEPES pH 7.5, and 100 mM NaCl). The proteins were cultured for 30 minutes, and the bimane spectra thereof were measured. The receptor dissolved in 0.1% DDM was diluted with the NH buffer, and used as the control. Data was presented as an average of three separate experiments performed in triplicate.

As shown in FIG. 21, it was confirmed that, when the amphipathic molecules were diluted so that the concentrations of the amphipathic molecules were reduced to a fiftieth of their individual CMCs and measured for the stability of $\beta_2$AR, the stability of the receptor was secured for a prolonged period of time in the case of all MNA-5, MNA-6, and MNA-7 compared to that of DDM, which indicates that MNA-5, MNA-6, or MNA-7 was detached from a surface of the membrane protein at a highly reduced rate because MNA-5, MNA-6, or MNA-7 was very strongly bound to the surface of the membrane protein.

<5-3>Measurement of Ligand (DHA) Binding Activity of mBBr-$\beta_2$AR Using Radioactive Ligand Binding Test The activity of the receptor (mBBr-$\beta_2$AR) dissolved in DDM or MNAs (MNA-5, MNA-6, or MNA-7) was measured by binding of [$^3$H]-dihydroalprenolol ([$^3$H]-DHA).

Specifically, a radioactive ligand binding test was performed using the following method. The $\beta_2$AR dissolved in 0.1% DDM was purified according to the method disclosed in the article by D. M. Rosenbaum et al. (*Science* 2007, 318, 1266-1273.) until the final concentration reached approximately 5 mg/mL (approximately 100 μM). The purified $\beta_2$AR was loaded onto an M1 Flag column in the presence of 2 mM CaCl$_2$, and the column was then washed with an MNA buffer (20 mM HEPES pH 7.5, 100 mM NaCl, and 0.2% MNA). Thereafter, the receptor was eluted into a 20×CMC concentration of MNA-5, MNA-6, or MNA-7 using 5 mM EDTA and 0.2 mg/ml of free Flag peptides. 0.1 pmol of the purified $\beta_2$AR dissolved in DDM or MNAs (MNA-5, MNA-6, or MNA-7) was cultured with 10 nM of radioactive DHA [$^3$H]-dihydroalprenolol (DHA) at room temperature (RT) for 30 minutes. The mixture was loaded onto a G-50 column, and a flow-through solution was collected in a binding buffer (20 mM HEPES supplemented with 0.5 mg/ml BSA pH 7.5, 100 mM NaCl), and filled with 15 mL of a scintillation fluid. The receptor-coupled [$^3$H]-DHA was measured using a scintillation counter (Beckman). Non-specific binding of the [$^3$H]-DHA was measured by adding 2 μM of alprenolol (Sigma) in the same binding reaction. The binding ratio of the [$^3$H]-DHA was determined on a column graph. Each experiment was performed in triplicate.

As shown in FIG. 22, it was revealed that the ligand binding activity of the receptor dissolved in MNA-6 or MNA-7 was similar or superior to that of the receptor dissolved in DDM.

From these results, it could be seen that $\beta_2$AR dissolved in MNA-6 or MNA-7 had its protein functions maintained well during a substitution of the amphipathic molecules.

<5-4>Size Exclusion Chromatography (SEC) Analysis

An SEC analysis was performed to determine the size of the protein-amphipathic molecule complex (i.e., a protein-detergent complex (PDC)) formed by DDM, MNA-6, or MNA-7.

Specifically, the $\beta_2$AR dissolved in DDM, MNA-6 or MNA-7 was used as a test sample in the same manner as used in Example 5-3. The sample was loaded onto a Superdex-200 10/300 GL column (GE Healthcare) at 0.5 ml/min, an innate tryptophane fluorescence signal was measured at an excitation wavelength of 295 nm and an emission wavelength of 345 nm. A running buffer includes 20 mM HEPES pH 7.5, 100 mM NaCl, and 20×CMC MNA-6 or MNA-7. A difference in retention volume of the protein samples means a difference in size of the protein-detergent complexes (PDCs) formed in the presence of the amphipathic molecules.

As shown in FIG. 23, it was revealed that the PDCs formed by MNA-6 or MNA-7 were smaller in size compared to those formed by DDM. Such excellent characteristics of MNA-6 or MNA-7 in terms of improved stability of the membrane protein, formation of small-sized PDCs, etc. are thought to promote the crystallization of the membrane protein, thereby facilitating the structure analysis of the membrane protein such as in X-ray crystallography. Also, it was confirmed that MNA-6 or MNA-7 was suitable for electron microscopic analysis of the membrane protein due to the characteristics such as strong binding to a surface of the protein, formation of small-sized PDCs, and improved protein stability. Therefore, a membrane protein analysis test was performed for MNA-6 or MNA-7 using an electron microscope.

<5-5>Electron Microscopy (EM) Analysis

A $\beta_2$AR protein analysis test was performed for DDM, MNA-6, or MNA-7 using an electron microscope.

Specifically, samples were prepared using the conventional negative staining protocol disclosed in the article by M. Ohi et al. (*Biol. Proced. Online* 2004, 6, 23-34.). In summary, 3 μL of $\beta_2$AR dissolved in DDM, MNA-6, or MNA-7 was pipetted onto a glow-discharged carbon-coated grid, and stained with 1% (w/v) uranyl formate. Thereafter, the $\beta_2$AR was imaged at room temperature by running a Morgagni 268(D) transmission electron microscope (FEI Company) at 100 kV. The images were recorded at 30,416× calibrated magnification using an Orius SC200W CCD camera (Gatan Inc.).

As shown in FIG. 24, it was revealed that the $\beta_2$AR dissolved in MNA-6 or MNA-7 had a uniform background clutter that were relatively smaller in quantity compared to the proteins dissolved in DDM.

From such results, it could be seen that the MNAs are able to be used to analyze a structure of the membrane protein under an electron microscope (EM).

The invention claimed is:

1. A composition for extracting, solubilizing, stabilizing or crystallizing a membrane protein, or analyzing a structure of the membrane protein using an electron microscope, the composition comprising a compound represented by the following Formula 1:

[Formula 1]

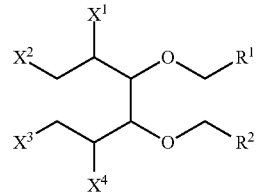

wherein $R^1$ and $R^2$ are each independently an unsubstituted $C_5$-$C_{20}$ alkyl group, a substituted or unsubstituted $C_5$-$C_{20}$ cycloalkyl group, or a substituted or unsubstituted $C_5$-$C_{20}$ aryl group; and $X^1$, $X^2$, $X^3$, and $X^4$ are each independently a glucose or maltose, whereby the composition is for extracting, solubilizing, stabilizing or crystallizing a membrane protein, or analyzing the structure of the membrane protein using the electron microscope.

2. The composition of claim 1, wherein each of $R^1$ and $R^2$ is $C_7$-$C_{18}$ alkyl group; $R^1$ and $R^2$ are the same.

3. The composition of claim 1, wherein the compound is represented by the following Formula 2, Formula 3, Formula 4, Formula 5, Formula 6, Formula 7, Formula 8, Formula 9, Formula 10, or Formula 11:

[Formula 2]

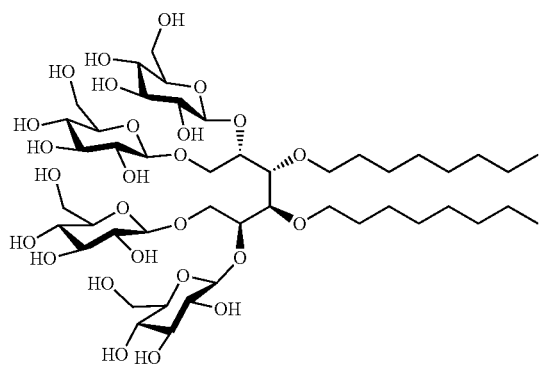

[Formula 3]

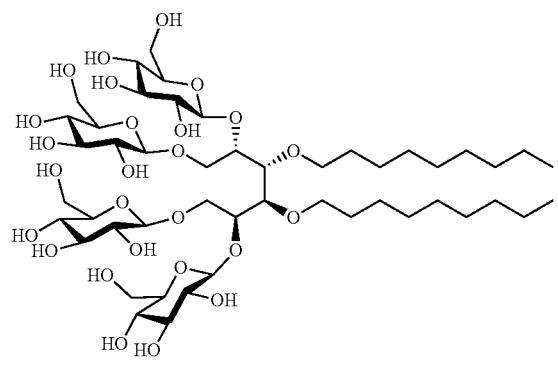

[Formula 4]

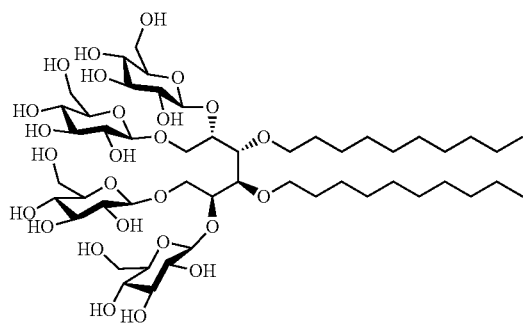

[Formula 5]

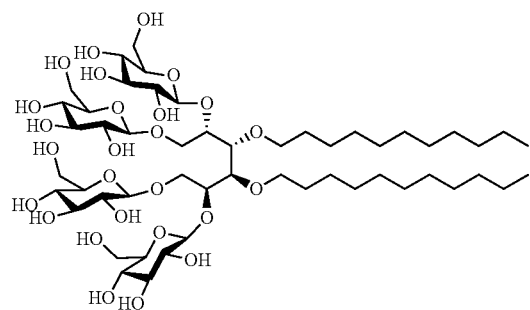

[Formula 6]
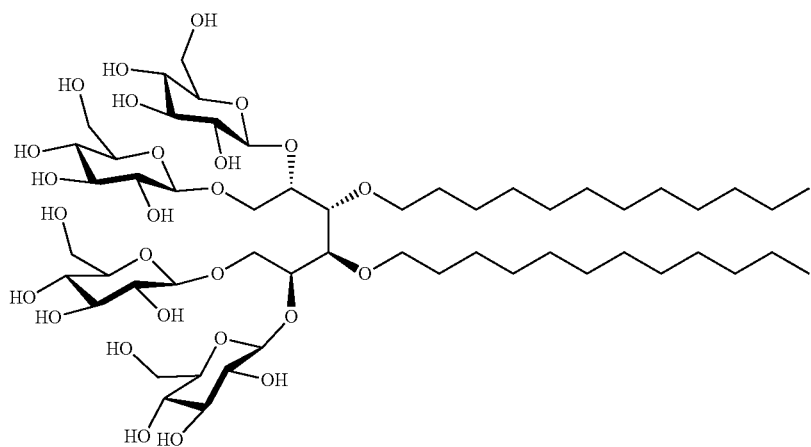
[Formula 7]
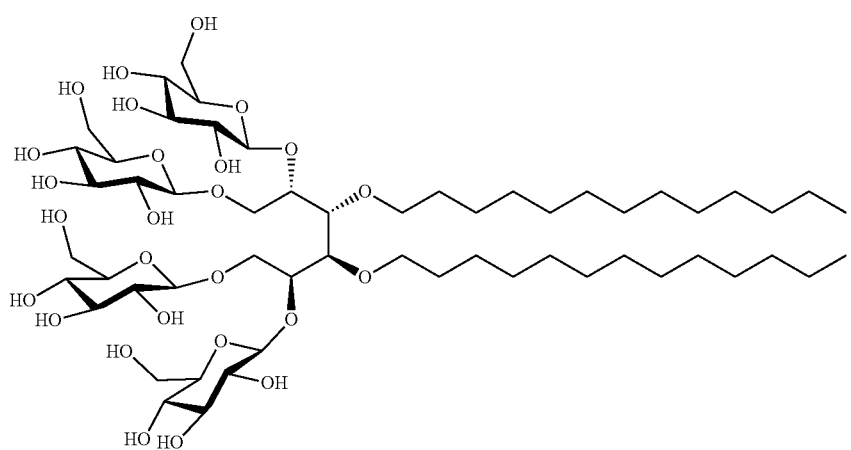
[Formula 8]
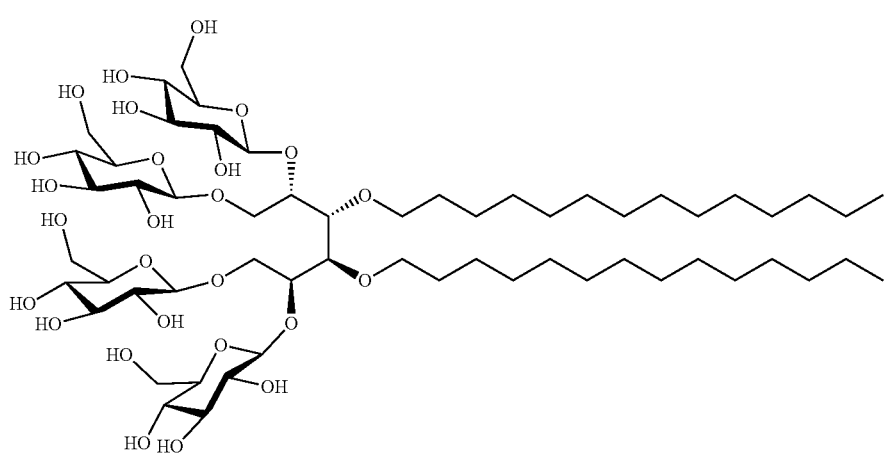

[Formula 9]

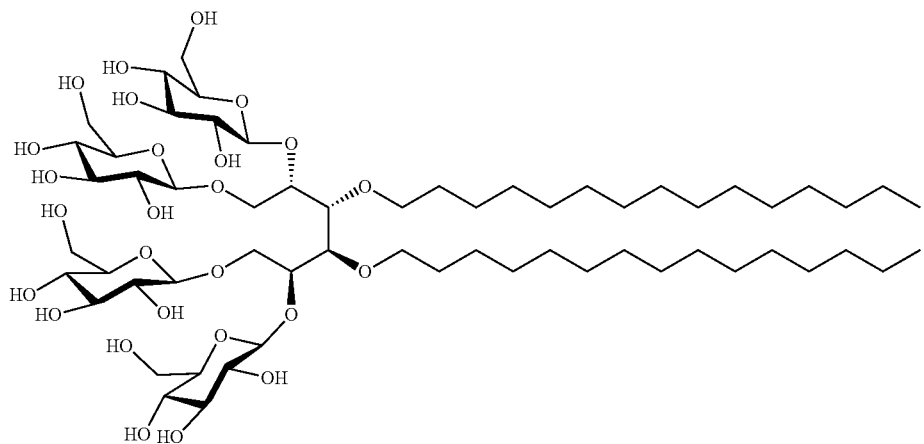

[Formula 10]

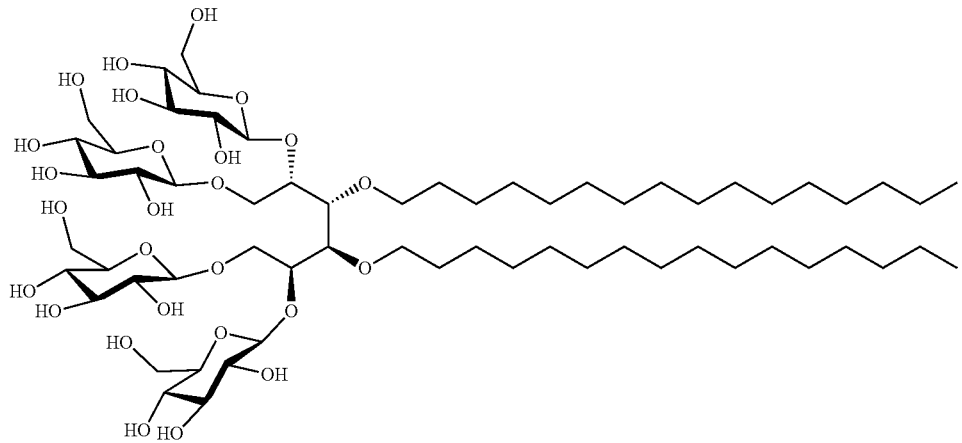

[Formula 11]

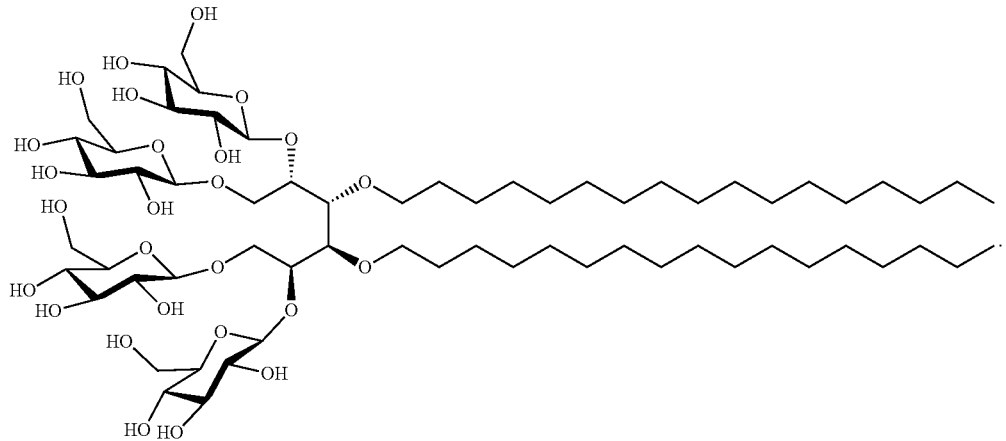

4. The composition of claim 1, wherein the compound is an amphipathic molecule for extracting, solubilizing, stabilizing or crystallizing a membrane protein.

5. The composition of claim 1, wherein the compound has a critical micellar concentration (CMC) of $1 \times 10^{-4}$ mM to 1.0 mM in an aqueous solution.

6. The composition of claim 1, wherein the compound is an amphipathic molecule capable of forming a complex with the membrane protein for analyzing a structure of the membrane protein using an electron microscope.

7. The composition of claim 1, wherein the composition is a micelle, a liposome, an emulsion, or a nanoparticle formulation.

* * * * *